United States Patent
Kim

(10) Patent No.: US 10,154,866 B2
(45) Date of Patent: Dec. 18, 2018

(54) MEDICAL INSERTING APPARATUS

(71) Applicant: KYUNGPOOK NATIONAL UNIVERSITY INDUSTRY-ACADEMIC COOPERATION FOUNDATION, Daegu (KR)

(72) Inventor: Kyoung Tae Kim, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 241 days.

(21) Appl. No.: 14/911,694

(22) PCT Filed: Aug. 19, 2014

(86) PCT No.: PCT/KR2014/007664
§ 371 (c)(1),
(2) Date: Feb. 11, 2016

(87) PCT Pub. No.: WO2015/030409
PCT Pub. Date: Mar. 5, 2015

(65) Prior Publication Data
US 2016/0199112 A1    Jul. 14, 2016

(30) Foreign Application Priority Data

Aug. 26, 2013 (KR) .......... 10-2013-0101078
Mar. 11, 2014 (KR) .......... 10-2014-0028345
(Continued)

(51) Int. Cl.
*A61B 17/86* (2006.01)
*A61B 17/17* (2006.01)
(Continued)

(52) U.S. Cl.
CPC .......... *A61B 17/864* (2013.01); *A61B 5/0492* (2013.01); *A61B 5/4836* (2013.01);
(Continued)

(58) Field of Classification Search
CPC . A61B 17/864; A61B 5/0492; A61B 17/1707; A61B 17/8635
See application file for complete search history.

(56) References Cited

U.S. PATENT DOCUMENTS 4,027,392 A * 6/1977 Sawyer .............. A61C 8/00
    433/174
4,027,932 A   6/1977 Kunkel et al.
(Continued)

FOREIGN PATENT DOCUMENTS

JP    2011-139901 A    7/2011
JP    2014-517739 A    7/2014
(Continued)

*Primary Examiner* — Christian Sevilla
(74) *Attorney, Agent, or Firm* — Novick, Kim & Lee, PLLC; Sang Ho Lee

(57) ABSTRACT

According to one embodiment, a medical insertion apparatus includes a screw nail body inserted into a human body and an electrode which is provided in the screw nail body and includes an externally exposed portion. Here, a through hole may be formed in the screw nail body or the electrode. According to one embodiment, a medical insertion apparatus includes a screw nail body inserted into a human body and an electrode which is provided in the screw nail body and exposed outside the screw nail body. Here, the screw nail body and the electrode may be provided as a combinable or separable structure. According to one embodiment, a medical insertion apparatus includes a screw nail body inserted into a human body, a driver engaged with the screw nail body to tighten or loosen the screw nail body, and a conductor portion which may be provided in the screw nail
(Continued)

body or the driver and may include an externally exposed portion.

14 Claims, 32 Drawing Sheets

(30) Foreign Application Priority Data

| Mar. 12, 2014 | (KR) | ........................ 10-2014-0028921 |
| Mar. 24, 2014 | (KR) | ........................ 10-2014-0034202 |
| Mar. 24, 2014 | (KR) | ........................ 10-2014-0034203 |
| Mar. 24, 2014 | (KR) | ........................ 10-2014-0034206 |
| Mar. 24, 2014 | (KR) | ........................ 10-2014-0034210 |

(51) Int. Cl.

| A61B 17/16 | (2006.01) |
| A61B 5/0492 | (2006.01) |
| A61B 17/70 | (2006.01) |
| A61B 5/00 | (2006.01) |
| A61N 1/05 | (2006.01) |
| A61B 17/90 | (2006.01) |
| A61B 18/00 | (2006.01) |
| A61C 8/00 | (2006.01) |
| A61C 19/04 | (2006.01) |
| A61N 1/36 | (2006.01) |
| A61B 17/00 | (2006.01) |

(52) U.S. Cl.
CPC ........ *A61B 5/4893* (2013.01); *A61B 17/1655* (2013.01); *A61B 17/1671* (2013.01); *A61B 17/1707* (2013.01); *A61B 17/70* (2013.01); *A61B 17/7032* (2013.01); *A61B 17/866* (2013.01); *A61B 17/8625* (2013.01); *A61B 17/8635* (2013.01); *A61B 17/8685* (2013.01); *A61N 1/0551* (2013.01); *A61B 2017/00022* (2013.01); *A61B 2017/0073* (2013.01); *A61B 2017/90* (2013.01); *A61B 2018/00339* (2013.01); *A61C 8/0022* (2013.01); *A61C 8/0089* (2013.01); *A61C 19/04* (2013.01); *A61N 1/0558* (2013.01); *A61N 1/36014* (2013.01)

(56) References Cited

U.S. PATENT DOCUMENTS

| 4,359,318 | A | * | 11/1982 | Gittleman | ............ A61C 8/0007 433/173 |
| 4,474,516 | A | | 10/1984 | Schiefer | |
| 4,678,383 | A | | 7/1987 | Bergner | |
| 5,127,407 | A | * | 7/1992 | Tan | ........................ A61B 5/031 356/41 |
| 5,265,504 | A | | 11/1993 | Fruhm | |
| 6,258,089 | B1 | | 7/2001 | Campbell et al. | |
| 6,290,701 | B1 | | 9/2001 | Enayati | |
| 6,402,757 | B1 | * | 6/2002 | Moore | ................. A61B 17/862 606/104 |
| 6,436,100 | B1 | * | 8/2002 | Berger | ................... A61B 17/60 411/394 |
| 6,652,525 | B1 | | 11/2003 | Assaker et al. | |
| 6,778,861 | B1 | * | 8/2004 | Liebrecht | ............... A61B 17/86 606/304 |
| 7,029,472 | B1 | | 4/2006 | Fortin | |
| 7,194,314 | B1 | * | 3/2007 | Richter | ............. A61N 1/36036 600/25 |
| 7,235,100 | B2 | | 6/2007 | Martinek | |
| 7,302,298 | B2 | * | 11/2007 | Lowry | ................. A61N 1/0531 607/116 |
| 7,662,154 | B2 | | 2/2010 | Ribeiro | |
| 8,057,521 | B2 | | 11/2011 | Smisson, III et al. | |
| 8,419,777 | B2 | | 4/2013 | Walker et al. | |
| 8,454,667 | B2 | | 6/2013 | Humphreys | |
| 8,628,325 | B2 | | 1/2014 | Vachtenberg | |
| 8,758,347 | B2 | | 6/2014 | Weiner et al. | |
| 8,906,077 | B2 | | 12/2014 | Bush, Jr. et al. | |
| 8,932,335 | B2 | | 1/2015 | Humphreys | |
| 8,940,030 | B1 | | 1/2015 | Stein et al. | |
| 9,265,531 | B2 | | 2/2016 | Ziolo | |
| 9,629,664 | B2 | | 4/2017 | Altarac et al. | |
| 9,775,652 | B2 | | 10/2017 | Altarac et al. | |
| 9,918,749 | B2 | | 3/2018 | Altarac et al. | |
| 9,918,760 | B2 | | 3/2018 | Bush, Jr. et al. | |
| 2002/0151899 | A1 | | 10/2002 | Bailey et al. | |
| 2003/0187440 | A1 | | 10/2003 | Richelsoph et al. | |
| 2004/0220571 | A1 | | 11/2004 | Assaker et al. | |
| 2004/0243207 | A1 | * | 12/2004 | Olson | ...................... A61N 1/05 607/116 |
| 2004/0267361 | A1 | | 12/2004 | Donnelly et al. | |
| 2005/0059972 | A1 | | 3/2005 | Biscup | |
| 2005/0192577 | A1 | | 9/2005 | Mosca et al. | |
| 2005/0261689 | A1 | | 11/2005 | Lin | |
| 2006/0161157 | A1 | | 7/2006 | Mosca et al. | |
| 2006/0217721 | A1 | | 9/2006 | Suh | |
| 2006/0235410 | A1 | | 10/2006 | Ralph et al. | |
| 2006/0247639 | A1 | | 11/2006 | Anderson | |
| 2006/0293670 | A1 | | 12/2006 | Smisson et al. | |
| 2007/0233071 | A1 | | 10/2007 | Dewey et al. | |
| 2008/0161864 | A1 | | 7/2008 | Beck et al. | |
| 2008/0221624 | A1 | | 9/2008 | Gooch | |
| 2009/0125072 | A1 | * | 5/2009 | Neubardt | ............ A61B 17/8625 606/305 |
| 2009/0318970 | A1 | | 12/2009 | Butler et al. | |
| 2010/0036467 | A1 | * | 2/2010 | Kraus | ...................... A61N 1/05 607/116 |
| 2010/0049256 | A1 | | 2/2010 | Jeon et al. | |
| 2010/0106198 | A1 | * | 4/2010 | Adcox | ............... A61B 17/8625 606/301 |
| 2010/0121383 | A1 | | 5/2010 | Stanaford et al. | |
| 2011/0022097 | A1 | | 1/2011 | Walker et al. | |
| 2011/0029023 | A1 | | 2/2011 | Tornier | |
| 2011/0106159 | A1 | | 5/2011 | Nazeck | |
| 2011/0144702 | A1 | | 6/2011 | Leroux et al. | |
| 2011/0230885 | A1 | | 9/2011 | Weiner et al. | |
| 2011/0264151 | A1 | | 10/2011 | Davis et al. | |
| 2012/0185001 | A1 | | 7/2012 | Nayet et al. | |
| 2012/0232595 | A1 | | 9/2012 | Holschlag | |
| 2012/0265258 | A1 | | 10/2012 | Garvey | |
| 2012/0271363 | A1 | | 10/2012 | Luxon et al. | |
| 2012/0289978 | A1 | | 11/2012 | Jacob | |
| 2013/0023936 | A1 | | 1/2013 | Altarac et al. | |
| 2013/0041413 | A1 | | 2/2013 | Sun | |
| 2013/0231704 | A1 | | 9/2013 | Larroque-Lahitette | |
| 2013/0304067 | A1 | | 11/2013 | Hess et al. | |
| 2013/0325074 | A1 | | 12/2013 | Ziolo | |
| 2014/0066997 | A1 | | 3/2014 | Humphreys | |
| 2015/0134013 | A1 | | 5/2015 | Paul | |
| 2015/0201982 | A1 | | 7/2015 | Altarac et al. | |
| 2015/0216573 | A1 | | 8/2015 | Chin et al. | |
| 2015/0230838 | A1 | | 8/2015 | Lazoglu et al. | |
| 2016/0166295 | A1 | | 6/2016 | Ziolo | |
| 2016/0206351 | A1 | | 7/2016 | Eom | |

FOREIGN PATENT DOCUMENTS

| KR | 1999-0035953 A | 5/1999 |
| KR | 10-2002-0082009 A | 10/2002 |
| KR | 1020040001287 A | 1/2004 |
| KR | 20-0367241 Y1 | 11/2004 |
| KR | 10-2005-0023111 A | 3/2005 |
| KR | 10-2007-0026472 A | 3/2007 |
| KR | 10-2007-0112200 A | 11/2007 |
| KR | 10-2008-0059920 A | 7/2008 |
| KR | 10-0850322 B1 | 8/2008 |
| KR | 10-2008-0105506 A | 12/2008 |
| KR | 10-0872529 B1 | 12/2008 |
| KR | 10-2009-0015933 A | 2/2009 |
| KR | 10-2009-0111774 A | 10/2009 |
| KR | 10-2010-0124709 A | 11/2010 |

(56) References Cited

FOREIGN PATENT DOCUMENTS

| | | |
|---|---|---|
| KR | 10-2012-0039622 A | 4/2012 |
| KR | 10-2012-0040309 A | 4/2012 |
| KR | 10-2012-0052265 A | 5/2012 |
| KR | 10-1142895 B1 | 5/2012 |
| KR | 10-2012-0057758 A | 6/2012 |
| KR | 10-2013-0004669 A | 1/2013 |
| KR | 10-2013-0015081 A | 2/2013 |
| KR | 10-2013-0016303 A | 2/2013 |
| KR | 10-1331429 B1 | 11/2013 |
| KR | 10-2014-0003938 A | 1/2014 |
| KR | 10-2014-0018796 A | 2/2014 |
| KR | 10-2014-0052320 A | 5/2014 |
| KR | 10-1413732 B1 | 7/2014 |
| KR | 10-2015-0120105 A | 10/2015 |
| WO | 2008/146981 A1 | 12/2008 |
| WO | 2009/105106 A2 | 8/2009 |

* cited by examiner

MEDICAL INSERTING APPARATUS

TECHNICAL FIELD

The present invention relates to a medical insertion apparatus, more particularly, to a medical insertion apparatus capable of being inserted into a human body more safely.

BACKGROUND ART

Medical insertion apparatuses may include, for example, a pedicle screw nail, a spine screw nail, a bone screw nail, a dental implant, etc.

Generally, patients with a fractured or partially damaged spine cannot perform in that state. Even though the degree of damage is not very serious and the person is capable of moving, their recovery is slow despite treatment because damaged or fractured parts of spine are pressurized by adjacent parts or in contact therewith.

Consequently, in the case of patients with a fractured or partially damaged spine, an operation is performed to support an adjacent spinal part using an artificial aid in order to keep pressure off of the fractured or damaged part of the spine.

Artificial aids for supporting the spine that are used in these cases may include pedicle screw nails inserted and installed either on top or bottom of the damaged part of the spine to function as an anchor with bands and rods connected through the respective pedicle screw nails to function as supporters.

Furthermore, certain pedicle screw nails are used in different pedicle screw nail insertion operations. A monoaxial screw head is designed to remain at a certain angle and stay immobile and a polyaxisal screw head is designed to have the ability to rotate.

The dental implant is inserted into the oral cavity tissue and acts much like osseous tissue to maintain and support prosthetic appliances and may be constructed to replace the dental root of a missing tooth.

In detail, in the case of dental implants, artificial dental roots made of biocompatible titanium are implanted into the alveolar bones so that artificial teeth can be connected to restore original tooth functions.

As treatments and operations related to the spine and teeth have recently increased, research on these devices that are inserted into the human body has also been vigorously performed.

For example, KR Patent Application No. 2012-0074355, filed on Jul. 9, 2012, discloses a pedicle screw nail which includes a screw pole provided with a through hole having a polygonal cross section and a head portion.

DISCLOSURE

Technical Problem

One aspect of the present invention is to provide a medical insertion apparatus capable of efficiently sensing a nerve and preventing neurological damage by increasing the contact area with the nerve.

One aspect of the present invention is to provide a medical insertion apparatus capable of increasing stability of movement and reducing a radiation exposure time during an operation.

One aspect of the present invention is to provide a medical insertion apparatus capable of being efficiently inserted into a human body using a guide element which guides insertion into the human body during an operation.

One aspect of the present invention is to provide a medical insertion apparatus accessible that is capable of sensing a nerve while forming a hole to insert a screw nail body because the screw nail body is formed as a tapping screw.

One aspect of the present invention is to provide a medical insertion apparatus in which an electrode is easily coupled with and separated from a screw nail body.

One aspect of the present invention is to provide a medical insertion apparatus in which a screw nail body and an electrode are able to be formed of materials with similar melting points.

One aspect of the present invention is to provide a medical insertion apparatus capable of reducing fraction defects, to have easier processing, and to reduce manufacturing costs by the assembly process processing in a way of assembling.

One aspect of the present invention is to provide a medical insertion apparatus in which the screw nail body or an electrode is easily maintained and repaired.

One aspect of the present invention is to provide a medical insertion apparatus capable of sensing contact with a nerve in real time to prevent neurological damage while being inserted into a human body.

One aspect of the present invention is to provide a medical insertion apparatus which one circuit is formed to sense a contact with another material, including a nerve, by using a short circuit.

One aspect of the present invention is to provide a medical insertion apparatus capable of assessing a material in contact with the screw nail body depending on a reduced amount of an electrical current.

One aspect of the present invention is to provide a medical insertion apparatus capable of analyzing whether a neurological contact is present by sensing an electromyogram (EMG).

One aspect of the present invention is to provide a medical insertion apparatus capable of sensing a surrounding nerve while forming a hole for inserting a screw nail body.

One aspect of the present invention is to provide a medical insertion apparatus capable of sensing a peripherally located nerve during the whole insertion process.

One aspect of the present invention is to provide a medical insertion apparatus capable of detecting the direction in which a nerve is located using an electrode focused on a certain direction.

One aspect of the present invention is to provide a medical insertion apparatus capable of checking the direction of an electrode while the driver rotates the screw nail body.

One aspect of the present invention is to provide a medical insertion apparatus capable of increasing the contact rate of the conductor segment through tractive forces of the screw nail body and a driver.

One aspect of the present invention is to provide a medical insertion apparatus capable of removing an abrasion phenomenon of the conductor portion caused by surface contact thereof.

One aspect of the present invention is to provide a medical insertion apparatus in which the conductor portion is able to be manufactured using various metals.

One aspect of the present invention is to provide a medical insertion apparatus capable of increasing the stability of operation and reducing the radiation exposure time during an operation.

One aspect of the present invention is to provide a medical insertion apparatus capable of being compatible with an existing nerve stimulating and monitoring apparatus without an additional device.

One aspect of the present invention is to provide a medical insertion apparatus which includes a receiver in the driver to wirelessly monitor a nerve.

One aspect of the present invention is to provide a medical insertion apparatus capable of reducing the amount of interruptions to the operator caused by wires.

One aspect of the present invention is to provide a medical insertion apparatus which includes a built-in battery included within the driver and mounted on a charging station to be easily charged.

Technical Solution

One aspect of the present invention provides a medical insertion apparatus including a screw nail body inserted into a human body and an electrode which is provided in the screw nail body and includes an externally exposed portion. Here, a through hole is able to be formed in the screw nail body or the electrode.

The through hole may extend from one end of the screw nail body to an end portion of the screw nail body along the longitudinal direction of the screw nail body.

A guide element which guides the insertion of the screw nail body into the human body may be to be located in the through hole.

When the electrode is located in a central portion of the screw nail body, the through hole may be formed in the central portion of the electrode.

The externally exposed portion of the electrode may be formed at the end portion of the screw nail body.

The externally exposed portion of the electrode may be formed at a point on the outer circumference of the screw nail body, spaced apart from an end portion of the screw nail body.

The externally exposed portion of the electrode may be formed in an annular shape along the outer circumference of the screw nail body.

The electrode may extend vertically or at a slant from the central portion of the screw nail body toward the outer circumference of the screw nail body.

The screw nail body may be formed as a tapping screw.

One aspect of the present invention provides a medical insertion apparatus including a screw nail body inserted into a human body and an electrode which is provided in the screw nail body and exposed outside the screw nail body. Here, the screw nail body and the electrode may be made to function combined or separate.

The electrode may be inserted through the end portion of the screw nail body and to be screw-coupled with the screw nail body.

The electrode may include a first portion which extends along the longitudinal direction of the screw nail body and a second portion connected to the first portion and exposed outward at the end portion of the screw nail body. Here, a screw thread may be formed on a part of the first portion.

A through hole for insertion of the first portion may be formed in the screw nail body, and a screw thread with the ability to couple with the screw thread of the first portion may be formed in the through hole.

The screw thread of the first portion and the screw thread of the through hole may be formed in positions adjacent to the end portion of the screw nail body.

When the first portion is screw-coupled with the through hole, one end of the first portion may be located at the same height of one end of the screw nail body.

The electrode may include a third portion which extends toward one side of the screw nail body along the longitudinal direction of the screw nail body and a fourth portion which is coupled with an end portion of the third portion and protrudes outward at the one side of the screw nail body.

To couple the third portion with the fourth portion, a concave element and a protruding element may be symmetrically formed at the third portion and the fourth portion, respectively.

The electrode may be inserted through one end of the screw nail body and to be screw-coupled with the screw nail body.

To restrict a separation after the screw nail body and the electrode are coupled, a guide groove and a guide protrusion may be symmetrically formed at the screw nail body and one end of the electrode.

One aspect of the present invention provides a medical insertion apparatus including a screw nail body capable of being inserted into a human body and a conductor portion which is provided in the screw nail body and includes an externally exposed portion. Here, the conductor portion extends along a longitudinal direction of the screw nail body and forms one closed loop.

The medical insertion apparatus may further include a driver engaged with the screw nail body to tighten or release the screw nail body. Here, the conductor portion may be disposed in the driver.

The conductor portion may include a first conductor which extends from one end of the screw nail body to the other end thereof and a second conductor which extends from the other end of the screw nail body to the one end thereof. Here, the first conductor and the second conductor may be connected to each other and a portion where the first conductor and the second conductor are connected may be exposed outward.

The conductor portion may include a third conductor connectable to the first conductor and a fourth conductor connectable to the second conductor. Here, the third conductor and the fourth conductor may be disposed spaced apart and may be disposed in the driver engaged with the screw nail body to tighten or release the screw nail body.

The medical insertion apparatus may further include a current generator which applies electric current to the third conductor and a current measurer which measures electric current which flows through the fourth conductor. Here, the current generator and the current measurer may be disposed in the driver.

The driver may include a monitor or a display including a lamp to check a change in electric current which flows through the conductor portion.

A groove or a protrusion for coupling with the driver may be formed at a top end of the screw nail body.

The externally exposed portion of the conductor portion may be formed along the outer circumference of the screw nail body and spaced apart from the end portion of the screw nail body in an annular shape.

The screw nail body may be formed as a tapping screw.

One aspect of the present invention provides a medical insertion apparatus including a screw nail body inserted into a human body and an electrode exposed outside the screw nail body. Here, the electrode extends from one end of the screw nail body to an end portion of the screw nail body along the longitudinal direction of the screw nail body.

The electrode may extend straight along the longitudinal direction of the screw nail body on an outer circumference of the screw nail body.

The electrode may be provided in a string shape which extends from a top end of the screw nail body to a central portion of the end portion of the screw nail body along an outer circumferential surface of the screw nail body.

The medical insertion apparatus may further include a driver engaged with the screw nail body to tighten or release the screw nail body. Here, the driver may have the ability to connect electrically with the electrode.

A groove for insertion of the driver may be formed at a top end of the screw nail body and the electrode may be connected to one side of the groove.

The driver may include an indicator element and the indicator element may be located in the same direction as the electrode.

The electrode may be formed by plating the outside of the screw nail body with a type of metal along the longitudinal direction of the screw nail body.

The electrode may be connected to a nerve stimulating and monitoring apparatus, and electric current which flows through the electrode may be sensed by the nerve stimulating and monitoring apparatus.

One aspect of the present invention provides a medical insertion apparatus including a screw nail body inserted into a human body, a driver engaged with the screw nail body to tighten or release the screw nail body, and a conductor portion which is provided in the screw nail body or the driver and includes an externally exposed portion.

The conductor portion may include a first conductor which is provided in the screw nail body and extends along a longitudinal direction of the screw nail body and a second conductor which is provided in the driver and extends along a longitudinal direction of the driver. Here, the first conductor and the second conductor may be in surface contact with each other.

The first conductor and the second conductor may be exposed outward in a position in which the screw nail body is in contact with the driver.

A groove into which an end of the driver is insertable may be formed at the screw nail body, and the first conductor and the second conductor may be electrically connected in the groove.

A protruding element for coupling with the driver may be formed at a top end of the screw nail body, and a screw thread may be formed on an inside of the protruding element.

A screw thread for screw-coupling with the protruding element may be formed on an outside of the driver.

The externally exposed portion of the conductor portion may be formed at an end portion of the screw nail body or at a point on an outer circumference of the screw nail body, spaced apart from the end portion of the screw nail body.

The externally exposed portion of the conductor portion may be formed on the whole outer circumference of the screw nail body.

One aspect of the present invention provides a medical insertion apparatus including a screw nail body inserted into a human body, a driver engaged with the screw nail body to tighten or release the screw nail body, and a conductor portion which is provided in the screw nail body and the driver and includes a portion exposed outward at one side of the screw nail body. Here, the screw nail body and the conductor portion disposed in the driver may be electrically connected to each other.

The medical insertion apparatus may further include a nerve stimulating and monitoring apparatus which transfers electrical stimulus to the conductor portion or may detect a signal caused by the electrical stimulus.

The driver and the nerve stimulating and monitoring apparatus may be connected to each other with or without wires.

The conductor portion may include an exposure terminal at one end of the driver and the nerve stimulating, and monitoring apparatus may be connected to the exposure terminal.

The medical insertion apparatus may further include a trigger device connected to the nerve stimulating and monitoring apparatus. Here, an end portion of the trigger device may be in contact with the exposure terminal.

The nerve stimulating and monitoring apparatus may include a transmitter, and the driver may include a receiver.

The driver may include a built-in battery.

A charging socket for charging the built-in battery may be mounted on one end of the driver.

The medical insertion apparatus may further include a charging station on which the charging socket is mountable to charge the built-in battery.

The conductor portion may include a first conductor which is provided in the screw nail body and extends along a longitudinal direction of the screw nail body and a second conductor which is provided in the driver and extends along a longitudinal direction of the driver. Here, the first conductor and the second conductor may be in contact with each other at one end of the screw nail body.

The externally exposed portion of the conductor portion may be formed at an end portion of the screw nail body or at a point on an outer circumference of the screw nail body, spaced apart from the end portion of the screw nail body.

The screw nail body may be formed as a tapping screw.

Advantageous Effects

According to one embodiment of the present invention, a medical insertion apparatus may efficiently sense a nerve and prevent neurological damage by increasing the contact area with the nerve.

According to one embodiment of the present invention, a medical insertion apparatus may increase the stability of operation and may reduce the radiation exposure time during an operation.

According to one embodiment of the present invention, a medical insertion apparatus may be efficiently inserted into a human body using a guide element during an operation.

According to one embodiment of the present invention, a medical insertion apparatus may sense a nerve while forming a hole to insert a screw nail body because the screw nail body is formed as a tapping screw.

According to one embodiment of the present invention, in a medical insertion apparatus, an electrode is easily coupled with or separated from a screw nail body.

According to one embodiment of the present invention, in a medical insertion apparatus, a screw nail body and an electrode may be formed of materials with similar melting points.

According to one embodiment of the present invention, in a medical insertion apparatus, fraction defective may be reduced, processing may be easily performed, and manufacturing costs may be reduced by processing in a way of assembling.

According to one embodiment of the present invention, in a medical insertion apparatus, the electrode or screw nail body is easily maintained and repaired.

According to one embodiment of the present invention, a medical insertion apparatus may sense contact with a nerve in real time and prevent neurological damage while being inserted into a human body According to one embodiment of the present invention, in a medical insertion apparatus, one circuit may be formed and may sense contact with another material including a nerve using a short circuit.

According to one embodiment of the present invention, a medical insertion apparatus may estimate a material in contact with a screw nail body depending on a reduced amount of an electrical current.

According to one embodiment of the present invention, a medical insertion apparatus may check whether neurological contact is present by sensing an electromyogram (EMG).

According to one embodiment of the present invention, a medical insertion apparatus may sense a surrounding nerve while forming a hole for inserting a screw nail body.

According to one embodiment of the present invention, a medical insertion apparatus may sense a peripherally located nerve during the whole insertion process.

According to one embodiment of the present invention, a medical insertion apparatus may detect the direction in which a nerve is located using an electrode formed in a certain direction.

According to one embodiment of the present invention, a medical insertion apparatus may check the direction of an electrode while a driver rotates a screw nail body.

According to one embodiment of the present invention, a medical insertion apparatus may increase the contact rate of a conductor portion through tractive forces of a screw nail body and a driver.

According to one embodiment of the present invention, a medical insertion apparatus may remove an abrasion phenomenon of a conductor portion caused by a surface contact thereof.

According to one embodiment of the present invention, in a medical insertion apparatus, a conductor portion may be manufactured using various metals.

According to one embodiment of the present invention, a medical insertion apparatus may increase the stability of operation and may reduce the radiation exposure time during an operation.

According to one embodiment of the present invention, a medical insertion apparatus may be compatible with an existing nerve stimulating and monitoring apparatus without an additional device.

According to one embodiment of the present invention, a medical insertion apparatus may include a receiver in the driver to wirelessly monitor a nerve.

According to one embodiment of the present invention, a medical insertion apparatus may reduce the amount of interruptions to the operator caused by wires.

According to one embodiment of the present invention, a medical insertion apparatus may include a built-in battery which is provided in the driver and mounted on a charging station to be easily charged.

MODE FOR INVENTION

Figure 1:
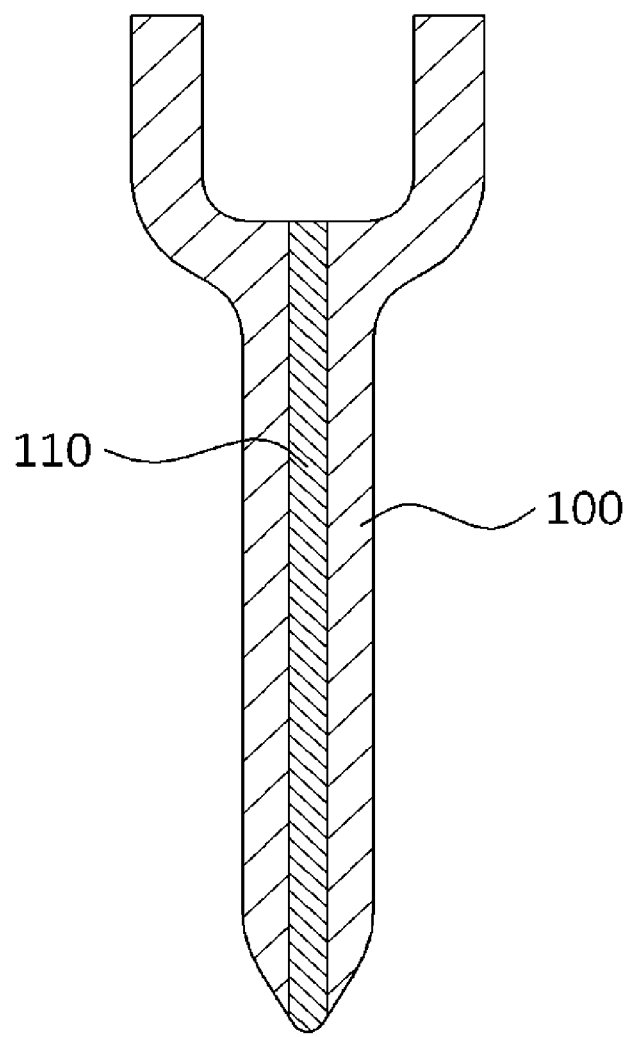
FIG. 1 illustrates a medical insertion apparatus according to a first embodiment of the present invention.

Hereinafter, embodiments of the present invention will be described in detail with reference to the attached drawings. However, the present invention is not restricted by or limited to the embodiments. Throughout the drawings, like reference numerals refer to like elements.

Figure 2A:
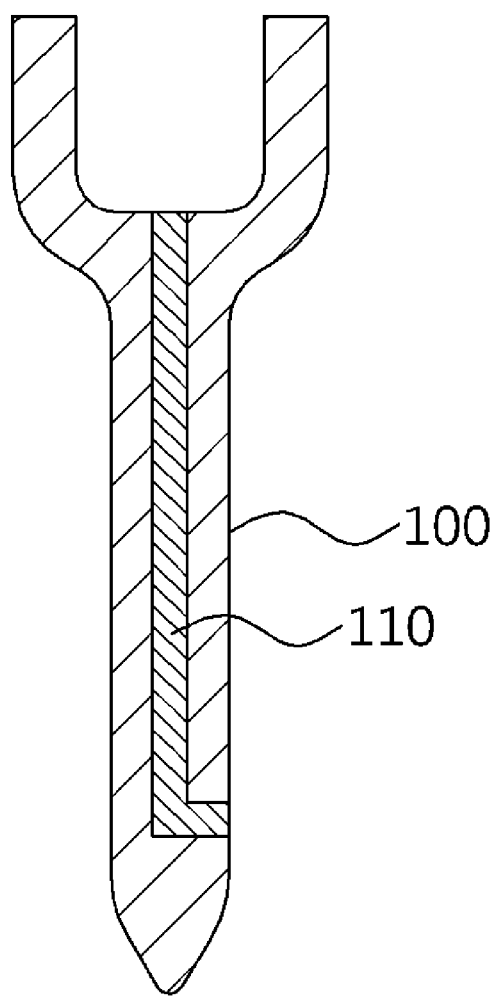
FIGS. 2a and 2b illustrate the states in which an electrode is capable of extending vertically or at a slant from the screw nail body in the medical insertion apparatus according to the first embodiment.
Figure 2B:
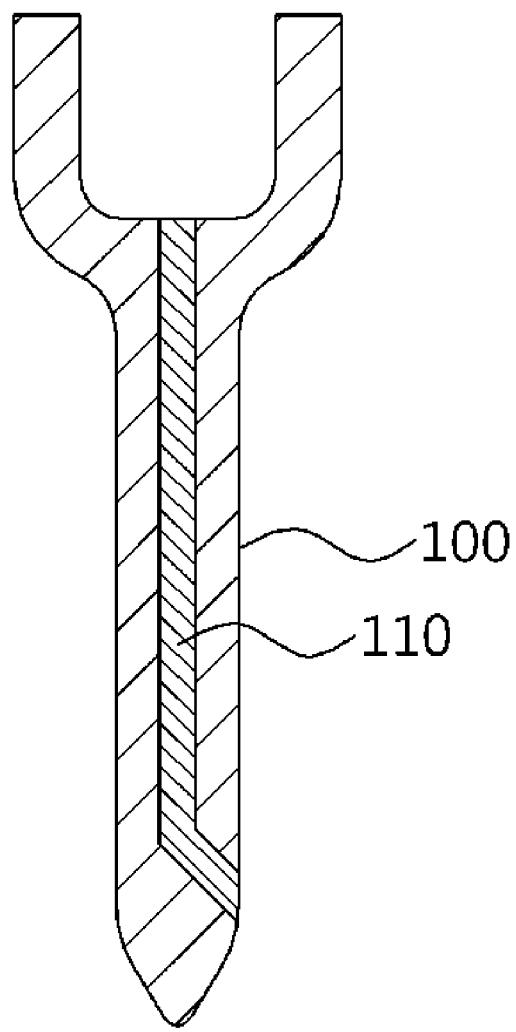
Figure 3A:
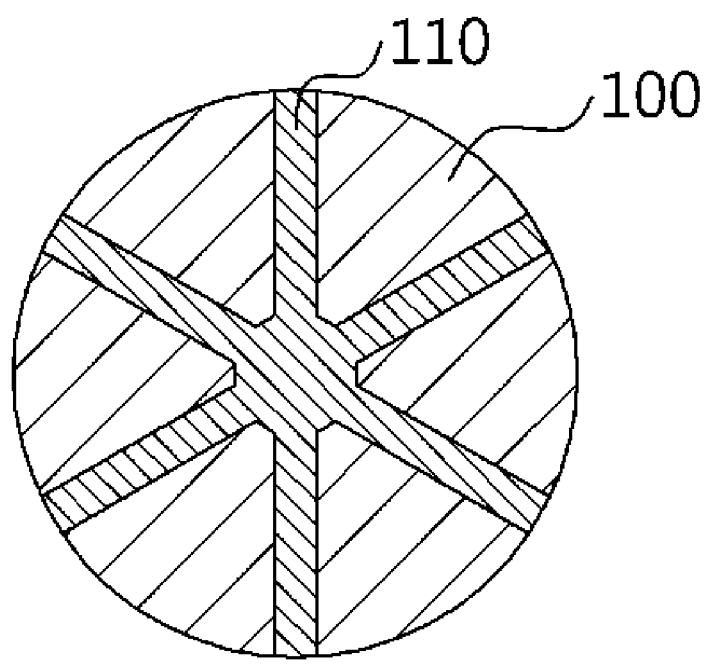
FIGS. 3a and 3b illustrates the states in which the electrode is exposed at a plurality of positions in the medical insertion apparatus according to the first embodiment.
Figure 3B:
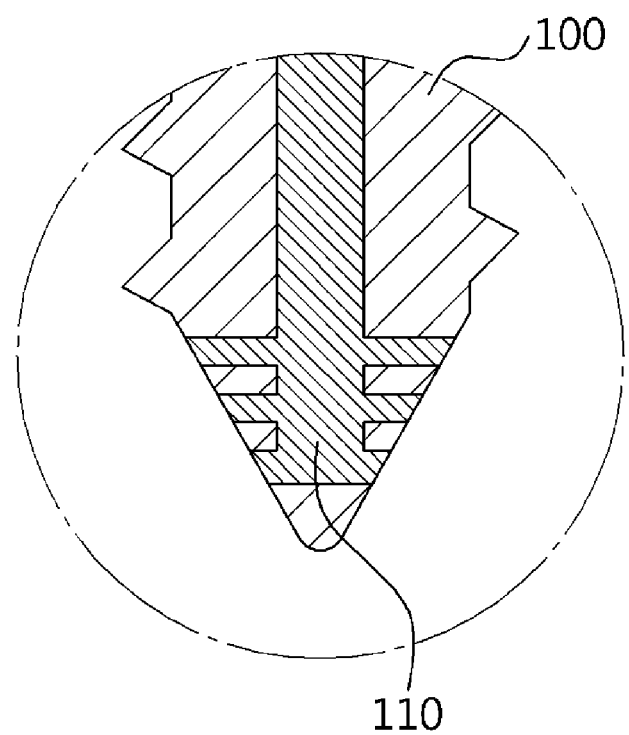
Figure 4:
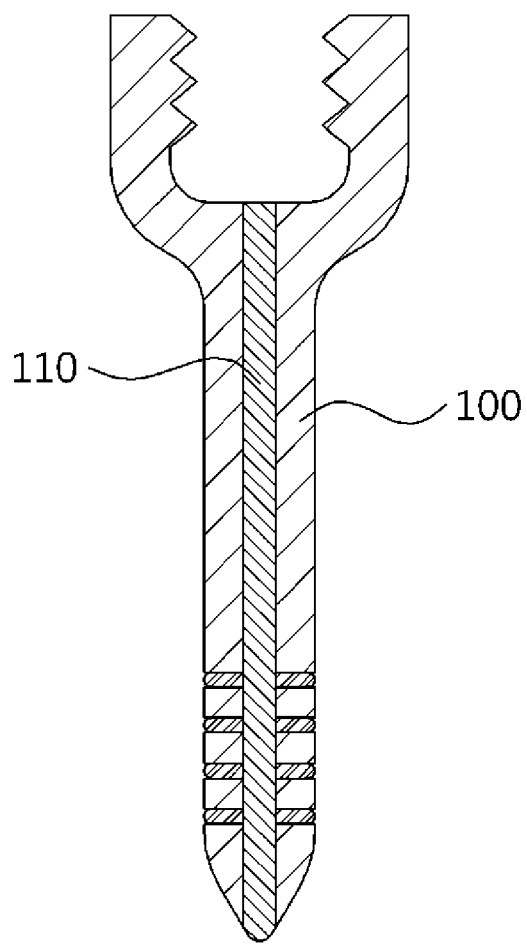
FIG. 4 illustrates a state in which an exposed part of the electrode is provided in an annular shape in the medical insertion apparatus according to the first embodiment.
Figure 5:
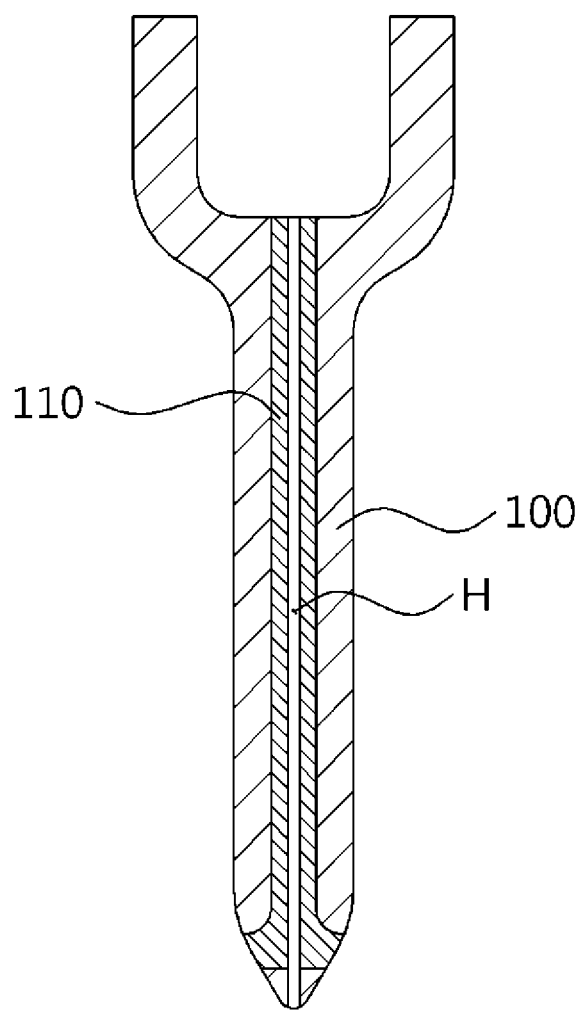
FIG. 5 illustrates a state in which a through hole is formed in the screw nail body or the electrode in the medical insertion apparatus according to the first embodiment.
Figure 6:
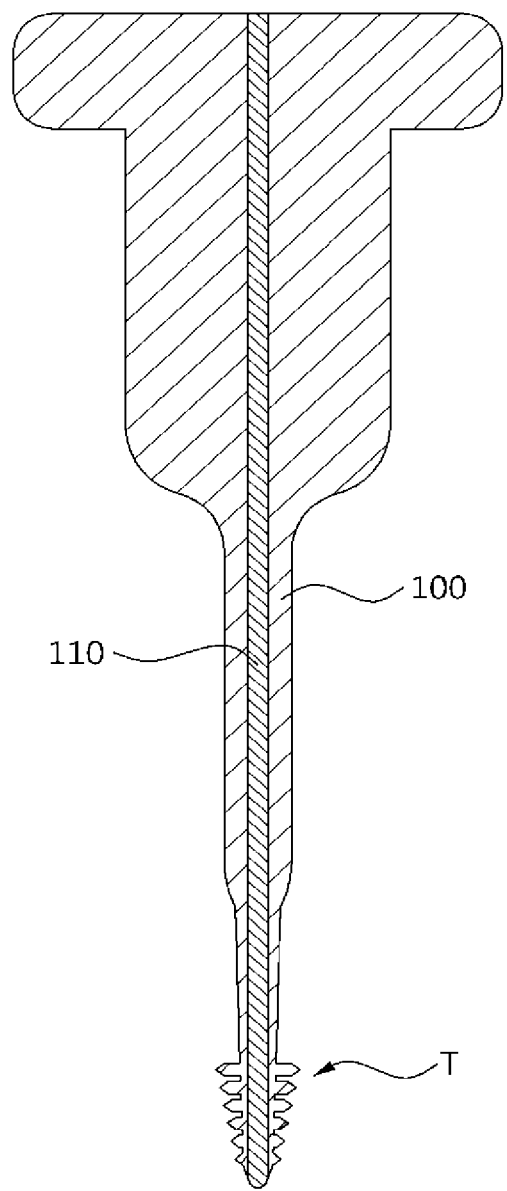
FIG. 6 illustrates a state in which the screw nail body is formed as a tapping screw in the medical insertion apparatus according to the first embodiment.

FIG. 1 illustrates a medical insertion apparatus according to the first embodiment. FIGS. 2a and 2b illustrate states in which an electrode is capable of extending vertically or at a slant from the screw nail body in the medical insertion apparatus according to the first embodiment. FIGS. 3a and 3b illustrate states in which the electrode is exposed at a plurality of positions in the medical insertion apparatus according to the first embodiment. FIG. 4 illustrates a state in which an exposed part of the electrode is provided in an annular shape in the medical insertion apparatus according to the first embodiment. FIG. 5 illustrates a state in which a through hole is formed in the screw nail body or the electrode in the medical insertion apparatus according to the first embodiment. FIG. 6 illustrates a state in which the screw nail body is formed as a tapping screw in the medical insertion apparatus according to the first embodiment.

Referring to FIG. 1, a medical insertion apparatus 10 according to the first embodiment may include a screw nail body 100 and an electrode 110.

The screw nail body 100 may be inserted into a human body and may include a screw thread formed on an outside thereof.

In detail, the screw nail body 100 may be inserted into the spine, teeth, or muscles. For example, the screw nail body 100 may be formed in a synostosis screw nail to be inserted into osseous tissue adjacent to a nerve, and more particularly, may be formed in a pedicle screw to be inserted into the spine, etc.

Accordingly, the screw nail body 100 may be manufactured using titanium which has excellent biocompatibility and strength to be used as a material for various implants The electrode 110 may be provided in a central portion of the screw nail body 100.

The electrode 110 may extend from one end of the screw nail body 100 toward an end portion of the screw nail body 100 along a longitudinal direction of the screw nail body 100.

In detail, a hole (not shown) which penetrates the screw nail body 100 from the one end to the end portion thereof may be provided in the central portion of the screw nail body 100 to dispose the electrode 110 therein.

Here, the electrode 110 may be formed by filling the hole with a melted material of electrode and solidifying the material through cooling at a room temperature.

For example, some protrusions or grooves may be formed in an inner circumferential surface of the hole and then the hole is filled with the melted material of electrode and the melted material may be solidified. In this case, the electrode 110 may be more strongly fixed to the hole, thereby being stably disposed in the screw nail body 100.

Here, the material of the electrode 110 may be platinum, gold, silver, tungsten, etc. and may be a material which has verified biocompatibility with a human body and excellent electrical conductivity to be appropriate for detecting a micro signal.

As shown in FIG. 1, the electrode 110 may be exposed outward at the end portion of the screw nail body 100.

Here, since the electrode 110 is exposed only at the end portion of the screw nail body 100, the medical insertion apparatus 10 according to the first embodiment may be relatively easily molded while being manufactured.

Also, since the electrode 110 is exposed at a portion which is the first one to be in contact with a nerve, the nerve may be initially sensed when the medical insertion apparatus 10 according to the first embodiment is inserted into the human body.

As shown in FIGS. 2a and 2b, the electrode 110 may be exposed at a position spaced apart from the end portion of the screw nail body 100 on an outer circumference of the screw nail body 100.

Particularly, referring to FIG. 2a, the electrode 110 may vertically extend from the center of the screw nail body 100 toward the outer circumference of the screw nail body 100.

In detail, the electrode 110 which extends along the longitudinal direction of the screw nail body 100 may vertically extend to the longitudinal direction of the screw nail body 100 and may be exposed outward on the outer circumference of the screw nail body 100 spaced apart from the end portion of the screw nail body 100.

Here, a distance between the electrode 110 located in the center of the screw nail body 100 and the end portion of the screw nail body 100 may be equal to a distance between an externally exposed portion of the electrode 110 and the end portion of the screw nail body 100.

Also, referring to FIG. 2a, the electrode 110 may slantly extend from the center of the screw nail body 100 toward the outer circumference of the screw nail body 100.

In detail, the electrode 110 which extends along the longitudinal direction of the screw nail body 100 may slantly extend to the longitudinal direction of the screw nail body 100 and may be exposed outward on the outer circumference of the screw nail body 100 spaced apart from the end portion of the screw nail body 100.

Here, a distance between the electrode 110 located at the center of the screw nail body 100 and the end portion of the screw nail body 100 may be greater or smaller than a distance between an externally exposed portion of the electrode 110 and the end portion of the screw nail body 100.

As described above, since the electrode 110 can be exposed outward at a point spaced apart from the end portion of the screw nail body 100, a range of monitoring nerves may be expanded.

Also, as shown in FIGS. 3a and 3b, the electrode 110 may be exposed at a plurality of positions.

Particularly, referring to FIG. 3a, the electrode 110 may be exposed outward in a radial shape at the outer circumference of the screw nail body 100.

In detail, the electrode 110 which extends along the longitudinal direction of the screw nail body 100 may vertically or slantly extend to the longitudinal direction of the screw nail body 100 and may be exposed outward on the outer circumference of the screw nail body 100 spaced apart from the end portion of the screw nail body 100.

Here, the electrode 110 may extend from the center of the screw nail body 100 toward the outer circumference of the screw nail body 100 in a radial direction.

Due to the electrode 110 configured as described above, the medical insertion apparatus 10 according to the first embodiment may monitor nerves in various aspects with respect to the screw nail body 100.

Also, referring to FIG. 3b, the electrode 110 may be exposed outward in a multi stage at the outer circumference of the screw nail body 100.

In detail, the electrode 110 which extends along the longitudinal direction of the screw nail body 100 may vertically or slantly extend to the longitudinal direction of the screw nail body 100 and may be exposed outward on the outer circumference of the screw nail body 100 spaced apart from the end portion of the screw nail body 100.

Here, the electrode 110 may extend from the center of the screw nail body 100 toward the outer circumference of the screw nail body 100 in a multi stage.

The electrode 110 is exposed outward in the multi stage only at the end portion of the screw nail body 100 in FIG. 3b but is not limited thereto. The electrode 110 may be exposed outward in various positions on the outer circumference of the screw nail body 100 in the multi stage.

Due to the electrode 110 configured as described above, the medical insertion apparatus 10 according to the first embodiment may efficiently monitor nerves at different heights with respect to the screw nail body 100.

Also, as shown in FIG. 4, the electrode 110 may be exposed outward in an annular ring shape.

Referring to FIG. 4, the electrode 110 may be not only exposed at the end portion of the screw nail body 100 but also exposed in the ring shape along the outer circumference of the screw nail body 100.

Here, an externally exposed portion of the electrode 110, provided in the ring shape, may be located at a point on the outer circumference of the screw nail body 100 spaced apart from the end portion of the screw nail body 100.

The externally exposed portion of the electrode 110, provided in the ring shape, may be integrally formed with the screw nail body 100 or may be separately formed from the screw nail body 100 to be detachable.

Also, a plurality of such ring shapes may be provided and may be arranged while being spaced apart in the longitudinal direction of the screw nail body 100.

The ring shape may be formed in a part of the screw nail body 100. For example, the ring shape may be formed in a half of the screw nail body 100.

Also, the ring shape may be formed in the whole screw nail body 100. Due to this, the electrode 110 may be exposed outward at the whole screw nail body 100.

Here, the electrode 110 which extends along the longitudinal direction of the screw nail body 100 may vertically or slantly extend to the longitudinal direction of the screw nail body 100 and may be connected to the externally exposed portion of the electrode 110, provided in the ring shape.

As described above, as the externally exposed portion of the electrode increases, a contact area with nerves may be increased and nerves may be more efficiently sensed. Accordingly, neurological damage may be prevented when the medical insertion apparatus 10 according to the first embodiment is inserted into the human body.

Also, referring to FIG. 5, a through hole H may be formed in a center of the screw nail body 100 or the electrode 110.

The through hole H may be formed from one end of the screw nail body 100 or the electrode 110 to the end portion of the screw nail body 100 along the longitudinal direction of the screw nail body 100 or the electrode 110. For example, the through hole H may be provided in a small hole or a tunnel shape with a diameter of about 1 mm.

In detail, when the electrode 110 extends from the one end of the screw nail body 100 in the longitudinal direction of the screw nail body 100 and is exposed outward at the outer circumference of the screw nail body 100 spaced apart from the end portion of the screw nail body 100, the through hole H may be formed while extending from the one end of the screw nail body 100 or the electrode 110 along the longitudinal direction of the screw nail body 100 or the electrode 110. Here, the through hole H may be straightly formed to penetrate through the electrode 110 and eventually to penetrate through the end portion of the screw nail body 100.

Otherwise, when the electrode 110 extends from the one end of the screw nail body 100 in the longitudinal direction of the screw nail body 100 and is exposed outward at the end portion of the screw nail body 100, the through hole H may be straightly formed to extend from the one end of the screw nail body 100 or the electrode 110 along the longitudinal direction of the screw nail body 100 or the electrode 110 and to penetrate through the end portion of the screw nail body 100 or the electrode 110.

At last, the through hole H may be formed not only at a center of the electrode 110 but also at the center of the screw nail body 100.

The electrode 110 is exposed outward at the outer circumference of the screw nail body 100 spaced apart from the end portion of the screw nail body 100 in FIG. 5 but is not limited thereto and may be exposed outward in various positions of the screw nail body 100 as described above.

A guide element (not shown) may be located in the through hole H formed in the electrode 110.

The guide element guides an insertion of the screw nail body 100 into the human body, and for example, may be provided as a wire, cable, or thread.

In detail, in a minimally invasive operation, a thin wire may be put into vertebrae and may pass through the through hole H of the screw nail body 100 or the electrode 110. After that, the screw nail body 100 may be inserted into a route of the wire.

Due to this, the insertion of the medical insertion apparatus 10 according to the first embodiment may be more easily performed and stability during an operation may be increased.

Also, referring to FIG. 6, the screw nail body 100 may be formed as a tapping screw T.

The tapping screw T may be used when a perforating process is previously performed before the screw nail body 100 is inserted into the human body.

Here, the screw nail body 100 may be more safely inserted through a hole provided by the tapping screw T.

Also, the electrode 110 is formed to be exposed outward on a side where the tapping screw T is formed, contact between the screw nail body 100 and nerves may be sensed during a perforating process.

The electrode 110 is exposed at the end portion of the screw nail body 100 in FIG. 6 but may be exposed at the outer circumference of the screw nail body 100 spaced apart from the end portion of the screw nail body 100.

As described above, the medical insertion apparatus 10 according to the first embodiment increases the contact area with nerves, thereby efficiently sensing nerves, preventing neurological damage, increasing stability during the operation, and reducing a radiation exposure time during the operation. Also, the medical insertion apparatus 10 may be efficiently inserted into the human body due to the guide element which guides the insertion into the human body during the operation. Also, since the screw nail body 100 is formed as a tapping screw, nerves may be sensed while a hole for inserting the screw nail body 100 is formed.

Figure 7:
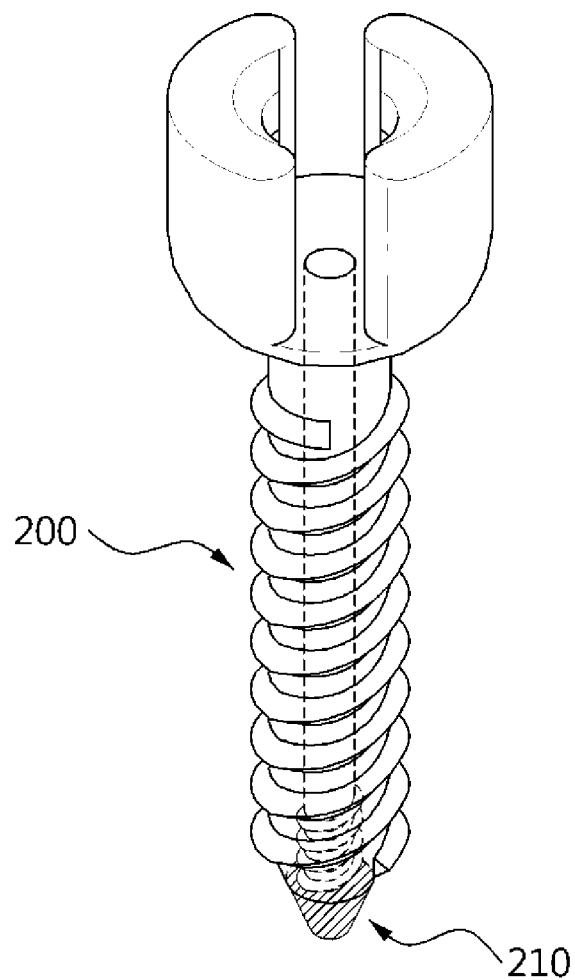
FIG. 7 illustrates the medical insertion apparatus according to a second embodiment of the present invention.
Figure 8:
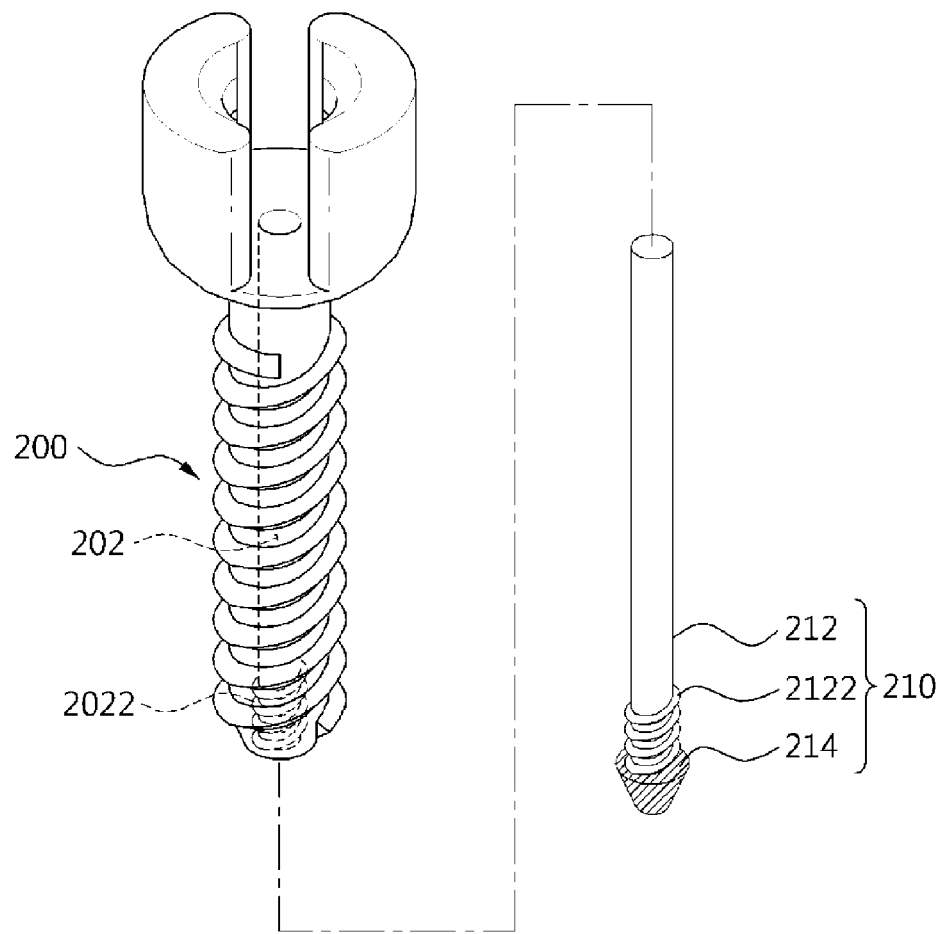
FIG. 8 illustrates a state in which an electrode is coupled with the screw nail body in the medical insertion apparatus according to the second embodiment.

FIG. 7 illustrates a medical insertion apparatus according to a second embodiment. FIG. 8 illustrates a state in which an electrode is coupled with a screw nail body in the medical insertion apparatus according to the second embodiment.

Referring to FIG. 7 or 8, a medical insertion apparatus 20 according to the second embodiment may include a screw nail body 200 and an electrode 210.

The screw nail body 200 may be inserted into a human body and may include a screw thread on an outside thereof.

In detail, the screw nail body 200 may be inserted into spine, teeth, or muscles. For example, the screw nail body 200 may be formed in a synostosis screw nail to be inserted into osseous tissue adjacent to a nerve, and more particularly, may be formed in a pedicle screw to be inserted into spine, etc.

Particularly, referring to FIG. 8, a through hole 202 may be formed in a center of the screw nail body 200.

Since the through hole 202 is for inserting the electrode 210, a shape of the through hole 202 may correspond to a shape of the electrode 210 located in the through hole 202.

For example, when a cross section of the electrode 210 located in the through hole 202 is a circular shape, a cross section of the through hole 202 may also be provided as a circular shape. Also, when the electrode 210 is provided as a cylindrical shape, the through hole 202 may also be provided as a cylindrical shape.

In detail, the through hole 202 may extend from one end of the screw nail body 200 toward an end portion of the screw nail body 200 along a longitudinal direction of the screw nail body 200.

Also, a screw thread 2022 may be formed in a position in the through hole 202, adjacent to the end portion of the screw nail body 200.

The screw thread 2022 formed in the through hole 202 is to be screw-coupled with a screw thread formed on the electrode 210, which will be described below in detail.

The electrode 210 may be inserted into the through hole 202.

The electrode 210 may be inserted into the through hole 202 through the end portion of the screw nail body 200.

In detail, the electrode 210 may be configured as follows.

The electrode 210 may include a first portion 212 which extends along the longitudinal direction of the screw nail body 200 and a second portion 214 connected to the first portion 212 and exposed at the end portion of the screw nail body 200.

The first portion 212 may be located in the through hole 202 of the screw nail body 200, and the second portion 214 may be exposed outward at the end portion of the screw nail body 200.

Accordingly, a shape of the first portion 212 may correspond to a shape of the through hole 202 and the second portion 214 may be formed to be greater than the through hole 202. Hereby, after the first portion 212 is inserted through the end portion of the screw nail body 200, the second portion 214 may be maintained as being exposed outward at the end portion of the screw nail body 200. Accordingly, the second portion 214 may not be inserted in the through hole 202.

Also, a screw thread 2122 capable of being coupled with the screw thread 2022 of the through hole 202 may be formed on the first portion 212.

The screw thread 2122 of the first portion 212 and the screw thread 2022 of the through hole 202 may be formed in positions corresponding to each other.

For example, the screw thread 2122 of the first portion 212 and the screw thread 2022 of the through hole 202 may be located adjacent to each other at the end portion of the screw nail body 200.

The second portion 214 may be exposed outward at the end portion of the screw nail body 200 and may sense, for example, contact between nerves or muscles and the electrode 210 when the screw nail body 200 is in contact with nerves or muscles.

Although not shown in detail in the drawings, the medical insertion apparatus 20 according to the second embodiment may be used while being connected to a nerve stimulating and monitoring apparatus.

The nerve stimulating and monitoring apparatus may include apparatuses for electromyography (EMG), evoked potential (EP), motor evoked potential (MEP), and somatosensory evoked potential (SSEP).

However, the nerve stimulating and monitoring apparatus is not limited thereto and may be any one which includes components for electrically stimulating muscles or nerves and receiving or detecting a signal caused by muscles or nerves due to the electrical stimulus.

In detail, the electrode 210 included in the medical insertion apparatus 20 according to the second embodiment may be connected to the nerve stimulating and monitoring apparatus and may directly apply a micro electrical current to nerves.

Accordingly, when the electrode 210 of the medical insertion apparatus 20 which is inserted during an operation or treatment is in contact with nerves, the electric current is applied to nerves to cause a signal at muscles or nerves. When the caused signal is detected by the nerve stimulating and monitoring apparatus, neurological contact of the medical insertion apparatus 20 according to the second embodiment may be known.

Here, the current may be transmitted to the second portion 214 through the first portion 212 and the second portion 214 may be in contact with muscles or nerves.

In detail, in the medical insertion apparatus 20 according to the second embodiment, the electrode 210 may be coupled with the screw nail body 200 as follows.

First, a top end of the first portion 212 of the electrode 210 may be inserted into the through hole 202 through the end portion of the screw nail body 200.

When the first portion 212 is inserted into the through hole 202 and then the second portion 214 protrudes from the end portion of the screw nail body 200, the screw thread 2022 of the through hole 202 and the screw thread 2122 of the first portion 212 may be in contact with each other.

Since a size of the second portion 214 is formed to be greater than a size of the through hole 202, the second portion 214 may not be inserted into the through hole 202 and may be in contact with the end portion of the screw nail body 200.

Here, the screw thread 2022 of the through hole 202 and the screw thread 2122 of the first portion 212 may be screw-coupled by driving the electrode 210 into the screw nail body 200.

As described above, when the screw nail body 200 and the electrode 210 are fastened to each other, the one end of the screw nail body 200 and one end of the first portion 212 may be located at the same height.

Also, the electric current may be transferred by the nerve stimulating and monitoring apparatus through an end portion of the first portion 212 exposed at the through hole 202.

On the contrary, in the medical insertion apparatus 20 according to the second embodiment, the electrode 210 may be separated from the screw nail body 200 as follows.

First, the electrode 210 may be drawn out from the screw nail body 200 in a direction opposite to a direction of driving the electrode 210 into the screw nail body 200 to fasten the screw nail body 200 with the electrode 210.

Hereby, screw-coupling between the screw thread 2022 of the through hole 202 and the screw thread 2122 of the first portion 212 may be released and then the first portion 212 may be drawn downward through the end portion of the screw nail body 200.

Since the size of the second portion 214 is formed to be greater than the size of the through hole 202, the second portion 214 may not be inserted into the through hole 202 and the first portion 212 may not be separated through the end portion of the screw nail body 200.

As described above, the screw nail body 200 and the electrode 210 may be easily coupled or separated.

Accordingly, in the medical insertion apparatus 20 according to the second embodiment, since it is unnecessary to insert a melted material of electrode in the screw nail body 200, the screw nail body 200 and the electrode 210 may be formed of materials having similar melting points. Also, fraction defective may be reduced through prefabrication, processing is easy, and total manufacturing costs may be reduced in a way of assembling.

As described above, the medical insertion apparatus 20 according to the second embodiment has been described. Hereinafter, a medical insertion apparatus 30 according to a third embodiment of the present invention or a medical insertion apparatus 40 according to a fourth embodiment of the present invention will be described and components similar to those of the medical insertion apparatus 20 according to the second embodiment will be omitted.

Figure 9:
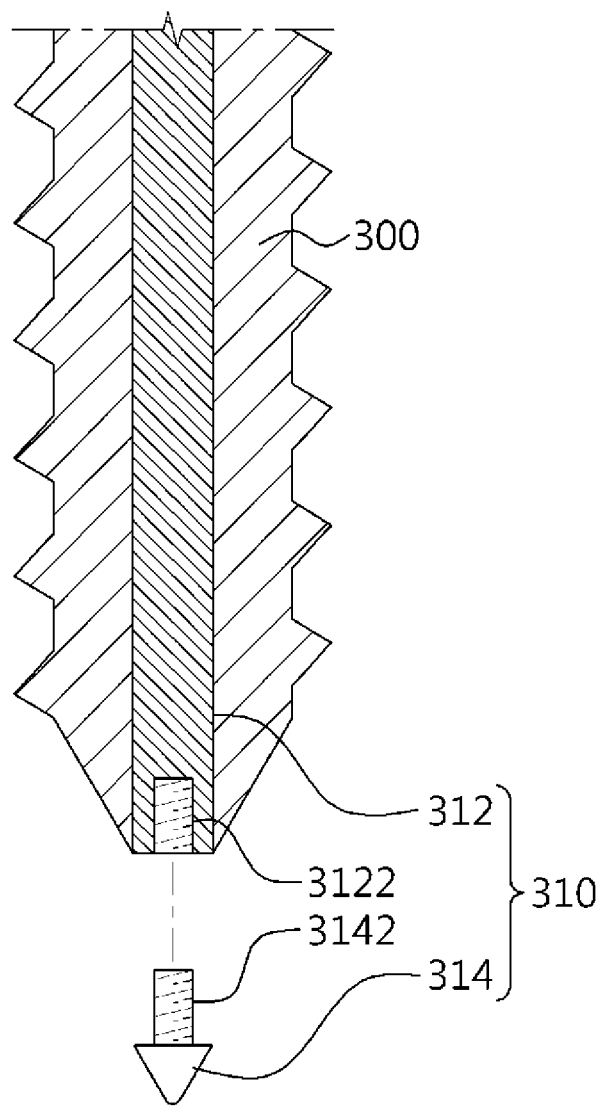
FIG. 9 illustrates a medical insertion apparatus according to a third embodiment of the present invention.

FIG. 9 illustrates a medical insertion apparatus according to a third embodiment of the present invention.

Referring to FIG. 9, the medical insertion apparatus 30 according to the third embodiment may include a screw nail body 300 and an electrode 310.

The medical insertion apparatus 30 according to the third embodiment is provided as a structure in which the electrode 310 is separable, unlike the medical insertion apparatus 20 according to the second embodiment.

In detail, the electrode 310 may include a third portion 312 and a fourth portion 314.

Here, the electrode 310 may be formed of platinum, gold, silver, tungsten, etc., which are biocompatible with a human body and has excellent electrical conductivity.

The third portion 312 may extend toward one side of the screw nail body 300 along a longitudinal direction of the screw nail body 300.

A concave element 3122 may be formed at an end portion of the third portion 312 located at an end portion of the screw nail body 300. This is to fasten the third portion 312 and the fourth portion 314 to each other. A screw thread may be formed on an inner surface of the concave element 3122.

The fourth portion 314 may protrude outward from the end portion of the screw nail body 300.

The fourth portion 314 is located at the end portion of the screw nail body 300 in FIG. 9 but is not limited thereto and may be located at a point spaced apart from the end portion of the screw nail body 300.

A protruding element 3142 may be formed at an end portion of the fourth portion 314 coupled with the third portion 312. This is to fasten the fourth portion 314 to the concave element 3122 of the third portion 312. A screw thread may be formed on an outer surface of the protruding element 3142.

As described above, the concave element 3122 formed in the third portion 312 of the electrode 300 and the protruding element 3142 formed on the fourth portion 314 may be formed symmetrically and the third portion 312 and the fourth portion 314 may be coupled with or separated from each other through screw-coupling therebetween.

However, the third portion 312 and the fourth portion 314 may be coupled through forcible fitting instead of screw-coupling.

Accordingly, since the medical insertion apparatus 30 according to the third embodiment is provided as a structure in which an externally exposed portion of the electrode 300 is replaceable, it is easy to maintain and repair the electrode 300.

Figure 10:
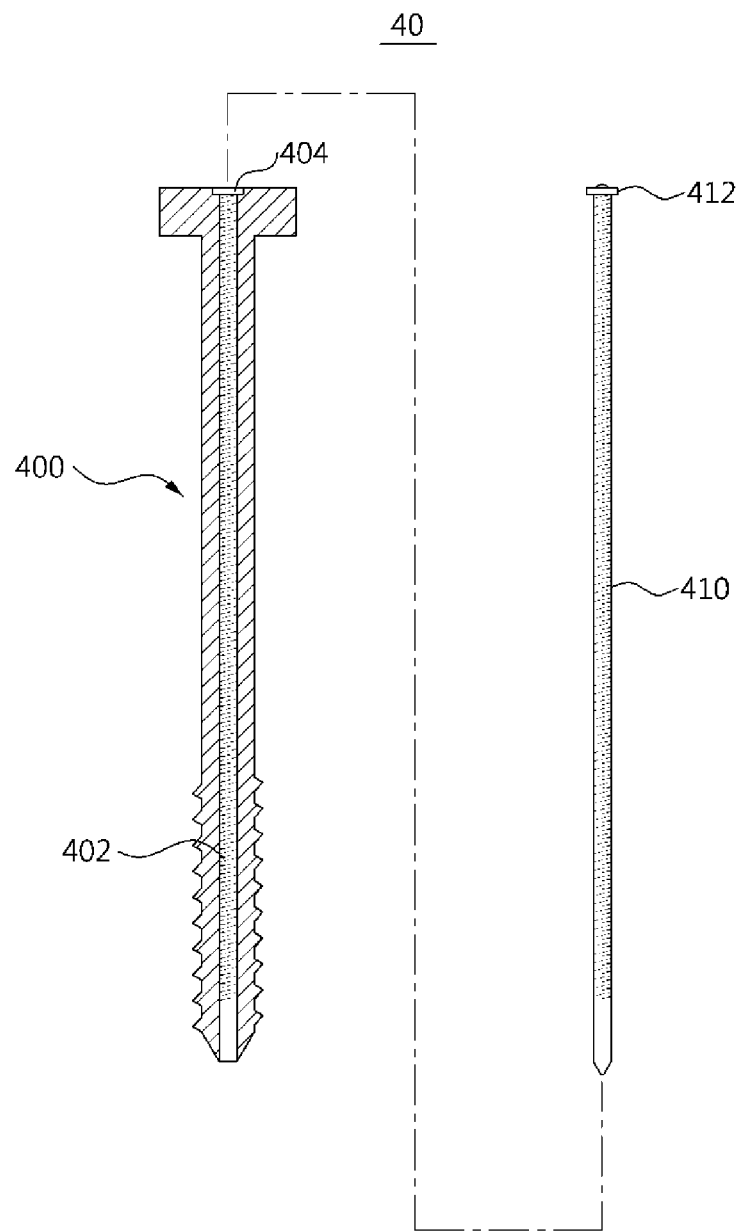
FIG. 10 illustrates a medical insertion apparatus according to a fourth embodiment of the present invention.

FIG. 10 illustrates a medical insertion apparatus according to a fourth embodiment of the present invention.

Referring to FIG. 10, a medical insertion apparatus 40 according to the fourth embodiment may include a screw nail body 400 and an electrode 410.

A through hole 402 for inserting the electrode 410 may be formed in the screw nail body 400.

In detail, the through hole 402 may extend from one end of the screw nail body 400 toward an end portion of the screw nail body 400 along a longitudinal direction of the screw nail body 400.

Here, a screw thread may be formed on an inner surface of the through hole 402. This is to be screw-coupled with a screw thread formed on an outer surface of the electrode 410 and thus may be formed corresponding to the screw thread formed on the outer surface of the electrode 410.

The electrode 410 may be inserted into the through hole 402 through the one end of the screw nail body 400. Here, the one end of the screw nail body 400 indicates a side opposite to the end portion of the screw nail body 400.

Here, the electrode 410 may be provided in a shape corresponding to the through hole 402 and may be exposed outward at the end portion of the screw nail body 400.

As described above, after the electrode 410 is screw-coupled with the through hole 402, to prevent the electrode 410 from being separated from the through hole 402, a guide groove 404 and a guide protrusion 412 may be symmetrically formed on one ends of the screw nail body 400 and the electrode 410, respectively.

The guide groove 404 is formed in the screw nail body 400 and the guide protrusion 412 is formed on the electrode 410 in FIG. 10. However, the guide protrusion 412 may be formed on the screw nail body 400 and the guide groove 404 may be formed in the electrode 410.

As described above, in the medical insertion apparatus according to the fourth embodiment, the screw nail body and the electrode are provided to be mutually coupled or separated, thereby easily coupling or separating the electrode with or from the screw nail body. Also, the screw nail body and the electrode may be formed of materials with similar melting points.

Figure 11:
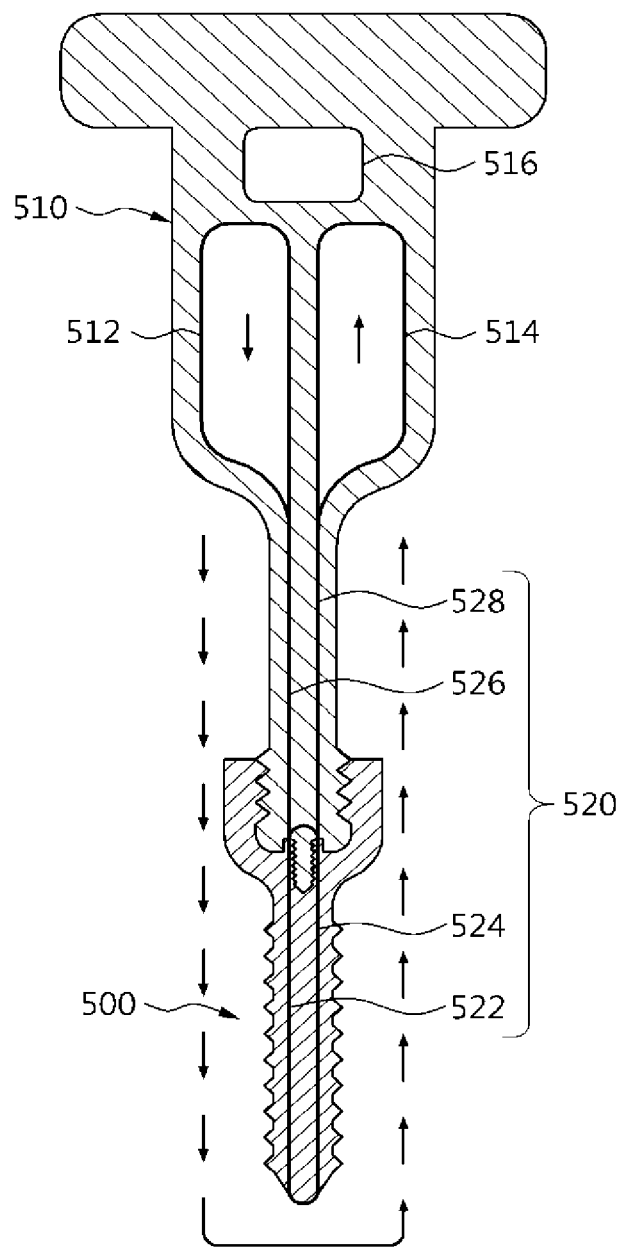
FIG. 11 illustrates a medical insertion apparatus according to a fifth embodiment of the present invention.

FIG. 11 illustrates a medical insertion apparatus according to a fifth embodiment of the present invention.

Figure 12:
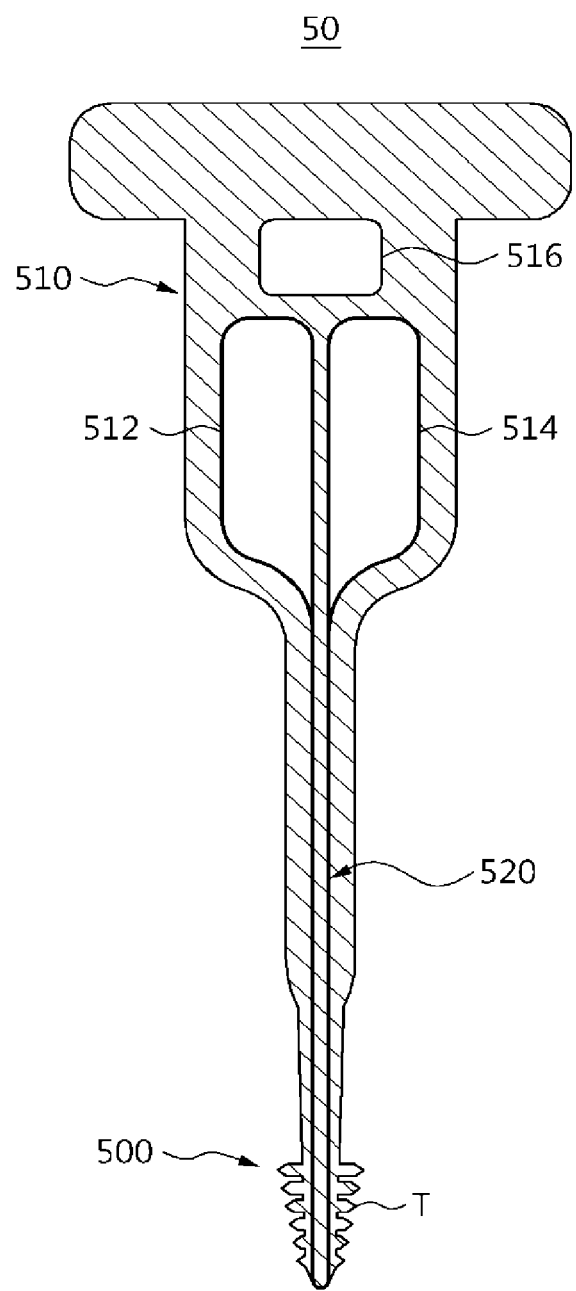
FIG. 12 illustrates a state in which a screw nail body is formed as a tapping screw in the medical insertion apparatus according to the fifth embodiment.

FIG. 12 illustrates a state in which a screw nail body is formed as a tapping screw in the medical insertion apparatus according to the fifth embodiment.

Figure 13A:
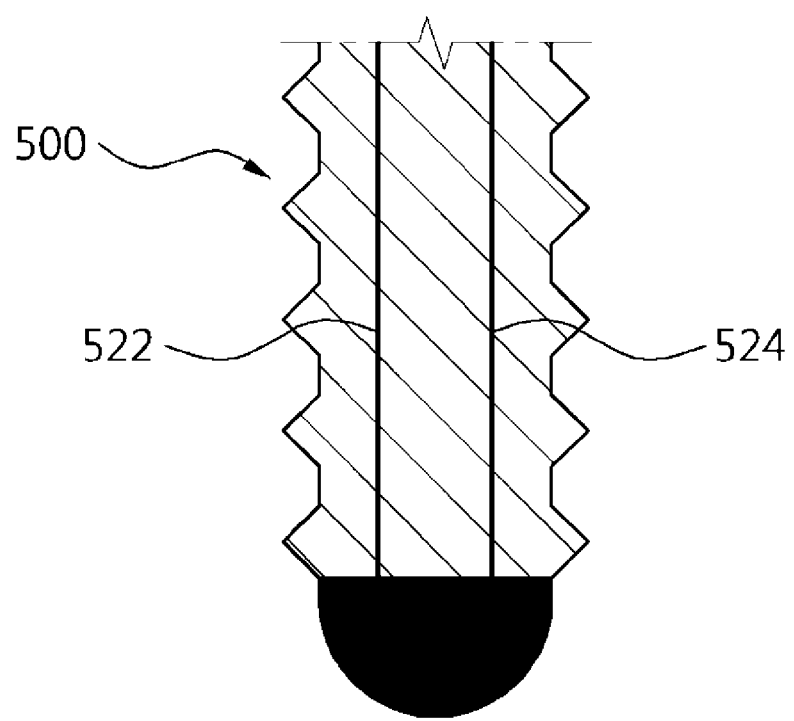
FIGS. 13a and 13b illustrate externally exposed portions of the screw nail body in the medical insertion apparatus according to the fifth embodiment.
Figure 13B:
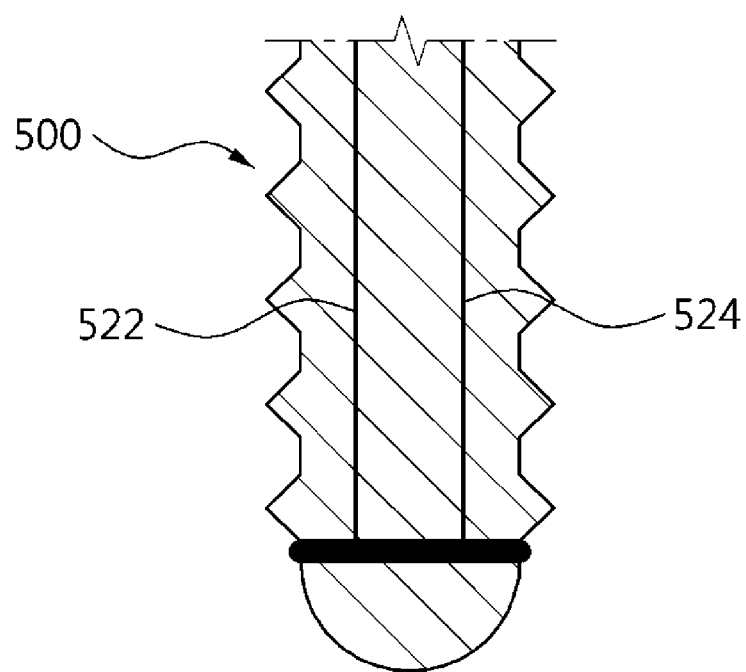

FIGS. 13a and 13b illustrate an externally exposed portion of the screw nail body in the medical insertion apparatus according to the fifth embodiment.

Figure 14:
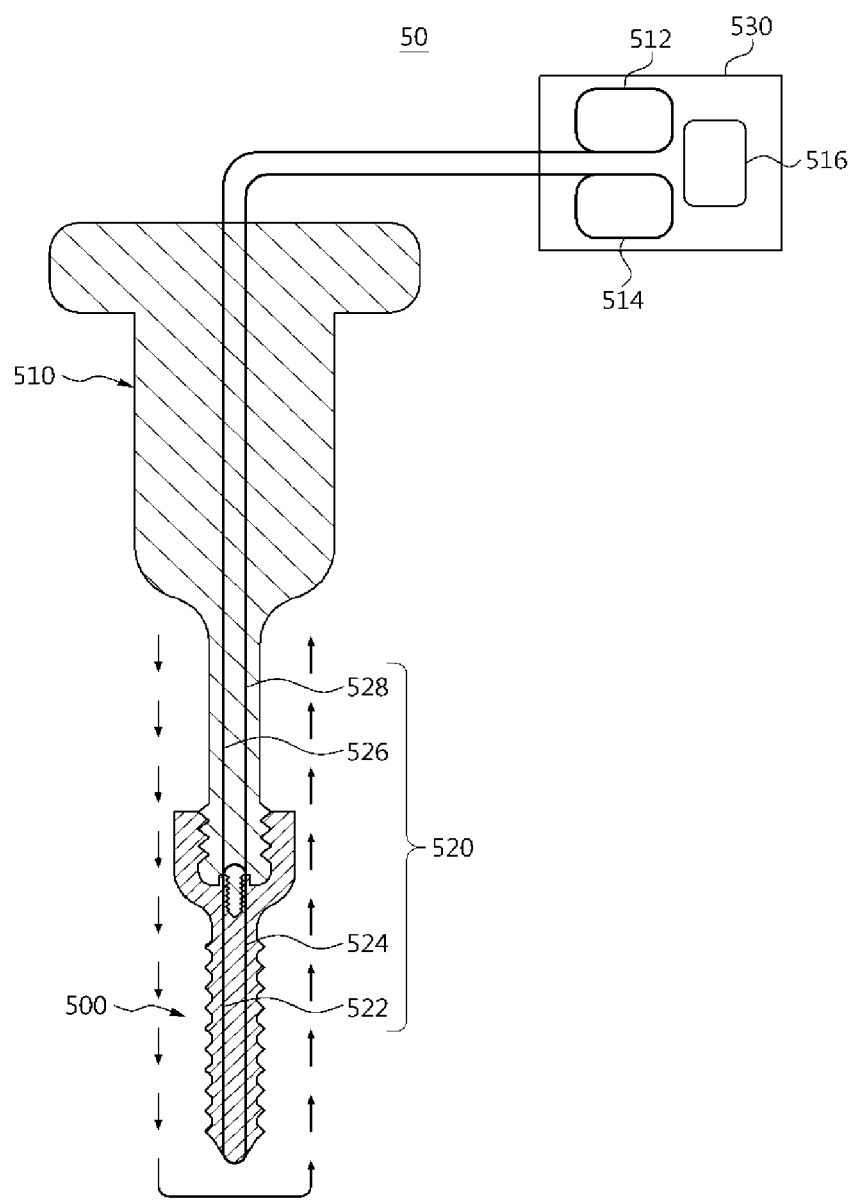
FIG. 14 illustrates a state in which the medical insertion apparatus according to the fifth embodiment is connected to an external terminal.

FIG. 14 illustrates a state in which the medical insertion apparatus according to the fifth embodiment is connected to an external terminal.

FIG. 11 illustrates the medical insertion apparatus according to the fifth embodiment, FIG. 12 illustrates a state in which the screw nail body is formed as the tapping screw in the medical insertion apparatus according to the fifth embodiment, FIGS. 13a and 13b illustrate the externally exposed portion of the screw nail body in the medical insertion apparatus according to the fifth embodiment, and FIG. 14 illustrates a state in which the medical insertion apparatus according to the fifth embodiment is connected to the external terminal.

Referring to FIG. 11, a medical insertion apparatus 50 according to the fifth embodiment may include a screw nail body 500, a driver 510, and a conductor portion 520.

The screw nail body 500 may be inserted into a human body and may include a screw thread on an outside thereof.

In detail, the screw nail body 500 may be inserted into spine, teeth, or muscles. For example, the screw nail body 500 may be formed in a synostosis screw nail to be inserted into osseous tissue adjacent to a nerve, and more particularly, may be formed in a pedicle screw to be inserted into spine, etc.

Accordingly, the screw nail body 500 may be manufactured using titanium which has excellent biocompatibility and strength to be used as a material for various implants.

To insert or remove the screw nail body 500 into or from the human body, the driver 510 may be engaged with a top of the screw nail body 500.

In detail, the driver 510 may be engaged with the screw nail body 500 to be tightened or released.

Here, the driver 510 may be screw-coupled with a top end of the screw nail body 500.

For example, a groove which includes a screw thread may be formed at the top of the screw nail body 500 and a protrusion which includes a screw thread may be formed at a bottom of the driver 510 corresponding to a shape of the groove. Otherwise, a protrusion which includes a screw thread may be formed at the top of the screw nail body 500 and a groove which includes a screw thread may be formed at the bottom of the driver 510 corresponding to a shape of the protrusion.

As described above, as the screw nail body 500 and the driver 510 rotate while being engaged with each other, the screw nail body 500 may be inserted into and fixed to the human body or may be separated therefrom.

Also, referring to FIG. 12, the screw nail body 500 may be formed as a tapping screw T. Here, the screw nail body 500 and the driver 510 may be integrally formed.

The tapping screw T may be used when a perforating process is previously performed before the screw nail body 500 is inserted into the human body.

Here, the screw nail body 500 may be more safely inserted through a hole provided by the tapping screw T.

When the screw nail body 500 and the driver 510 are integrally formed, a battery may be built in the medical insertion apparatus 50 according to the fifth embodiment to charge the medical insertion apparatus 50 according to the fifth embodiment to use.

Referring to FIG. 11 again, the conductor portion 520 may be disposed in the screw nail body 500 and the driver 510.

The conductor portion 520 may extend along a longitudinal direction of the screw nail body 500 and may form one closed loop.

Here, the conductor portion 520 may be formed of platinum, gold, silver, tungsten, etc., which has verified biocompatibility with a human body and excellent electrical conductivity to be appropriate for detecting a micro electromyogram (EMG) signal.

In detail, the conductor portion 520 may include a first conductor 522, a second conductor 524, a third conductor 526, and a fourth conductor 528.

The first conductor 522 may extend from the top end of the screw nail body 500 toward a bottom end thereof, and the second conductor 524 may extend from the bottom end of the screw nail body 500 toward the top end thereof.

Here, the first conductor 522 and the second conductor 524 may be connected to each other to form a closed loop.

Also, the first conductor 522 and the second conductor 524 may include a portion exposed outward at an end portion of the screw nail body 500.

The portion of the first conductor 522 and the second conductor 524, exposed outward at the end portion of the screw nail body 500, may sense nerves around the screw nail body 500.

Particularly, referring to FIGS. 13a and 13b, the closed loop of the first conductor 522 and the second conductor 524 may be exposed outward at the end portion of the screw nail body 500 as follows.

Referring to FIG. 13a, the exposed portion of the conductor portion 520 may be formed along an outer circumference of the screw nail body 500.

In detail, an additional member which surrounds the whole end portion of the screw nail body 500 may be provided or a part of the closed loop of the first conductor 522 and the second conductor 524 may be formed to surround the whole end portion of the screw nail body 500.

Due to this, an area in which the conductor portion 520 is in contact with nerves at the end portion of the screw nail body 500 may be increased, thereby more easily sensing nerves.

Also, referring to FIG. 13b, the exposed portion of the conductor portion 520 may be provided in a ring shape.

For example, an additional member provided in a ring shape may be mounted while being spaced apart from the end portion of the screw nail body 500. Here, the additional member provided in the ring shape may be electrically connected to the closed loop of the first conductor 522 and the second conductor 524.

Although one ring is mounted on the screw nail body 500 in the drawing, a plurality of such rings may be mounted on the screw nail body 500 while being spaced apart at intervals.

As described above, since the conductor portion 520 is exposed in a ring shape at a side of the screw nail body 500, the screw nail body 500 may sense nerves located on the side of the screw nail body 500 as being inserted into the human body.

Also, combining examples shown in FIGS. 13a and 13b, the conductor portion 520 may be configured to sense nerves at both the bottom end and side of the screw nail body 500.

The closed loop of the first conductor 522 and the second conductor 524 described above may include a portion exposed outward at the top end of the screw nail body 500.

The portion of the first conductor 522 and the second conductor 524, exposed outward at the top of the screw nail body 500, may be electrically connected to the conductor portion 520 disposed in the driver 510.

However, the closed loop formed by the first conductor 522 and the second conductor 524 may be disposed in the screw nail body 500.

Here, to electrically connect the closed loop of the first conductor 522 and the second conductor 524 to the conductor portion 520 disposed in the driver 510, a path for the conductor portion 520 may be formed in the screw nail body 500.

Also, the third conductor 526 may extend from a top end of the driver 510 toward a bottom end thereof, and the fourth conductor 528 may extend from the bottom end of the driver 510 toward the top end thereof.

Here, the third conductor 526 may be connected to the first conductor 522, and the fourth conductor 528 may be connected to the second conductor 524. Alternatively, the third conductor 526 may be connected to the second conductor 524, and the fourth conductor 528 may be connected to the first conductor 522.

Due to this, the third conductor 526 and the fourth conductor 528 may be disposed in the driver 510 while being spaced apart from each other.

As described above, the third conductor 526 and the fourth conductor 528 may be connected to the part of the closed loop of the first conductor 522 and the second conductor 524, respectively.

The third conductor 526 and the fourth conductor 528 may be connected with a current generator 512 and a current measurer 514, respectively.

The current generator 512 is an apparatus for applying an electrical current to the third conductor 526 and may transmit a certain amount of an electrical current to the third conductor 526.

The current measurer 514 may measure an electrical current which flows through the fourth conductor 528.

Here, the current generator 512 and the current measurer 514 may be disposed in the driver 510, like the third conductor 526 and the fourth conductor 528.

However, as shown in FIG. 14, the current generator 512 and the current measurer 514 may be provided in an external terminal 530. In detail, the third conductor 526 and the fourth conductor 528 may be exposed outward through the top end of the driver 510 to be connected to the current generator 512 and the current measurer 514 of the external terminal 530, respectively.

In this case, it is useful to maintain or repair defects which occur in the current generator 512 and the current measurer 514.

As described above, the conductor portion 520, the current generator 512, and the current measurer 514 may form one circuit.

In detail, when an electrical current is applied from the current generator 512 to the third conductor 526 like an arrow shown in FIG. 11, the electrical current may be transferred from the third conductor 526 to the closed loop of the first conductor 522 and the second conductor 524.

That is, the electrical current flows to the end portion of the screw nail body 500 along the longitudinal direction of the screw nail body 500 and turns at the end portion of the screw nail body 500 and flows again to the top of the screw nail body 500.

Here, the second conductor 524 is connected with the fourth conductor 528 and the fourth conductor 528 is connected with the current measurer 514, thereby measuring an electrical current which flows through the second conductor 524.

For example, when a 10 A electrical current is applied from the current generator 512 to the closed loop of the first conductor 522 and the second conductor 524 and a 5 A electrical current is measured by the current measurer 514, it means that the closed loop leak the electrical current.

In detail, the closed loop of the first conductor 522 and the second conductor 524 include the portion exposed outward at the end portion of the screw nail body 500. When the exposed portion is in contact with, for example, nerves, the electrical current may leaks through nerves. This is a principal similar to a short circuit.

Due to the principal, when the screw nail body 500 is inserted into the human body and is in contact with another material which includes nerves, the contact between the screw nail body 500 and nerves may be sensed due to a reduction of an electrical current.

Accordingly, when nerves are present around a fractured bone and in contact with the screw nail body 500, since contact between the screw nail body 500 and nerves is sensed, the screw nail body 500 may be inserted while avoiding nerves and may fix the fractured bone.

On the contrary, since a reduction amount of an electrical current may be different in a case of being in contact with nerves and a case of being in contact with muscles, it is possible to estimate which material is in contact in detail using the reduction amount of an electrical current.

Also, although not shown in the drawing in detail, an electrical current which leaks through nerves may cause an EMG signal at muscles. When the EMG signal caused at the muscles is detected by a muscle stimulus detector (not shown), the contact between the screw nail body 500 and nerves may be known through this.

As described above, a reduction of electrical current in the conductor portion 520 which forms a closed loop may be checked through the current measurer 514 or the muscle stimulus detector.

Also, the driver 510 may include a display 516 which includes a monitor or a lamp.

The reduction of an electrical current may be visually checked through the display 516.

In detail, when an electrical current applied by the current generator 512 to the conductor portion 520 and an electrical current measured by the current measurer 514 are displayed on the display 516, it may be easily checked whether an electrical current is reduced.

In addition, when the electrical current measured by the current measurer 514 is smaller than the electrical current applied by the current generator 512 to the conductor portion 520, the lamp is allowed to be turned on, thereby easily checking whether the electrical current is reduced.

Alternatively, when the electrical current measured by the current measurer 514 is smaller than the electrical current applied by the current generator 512 to the conductor portion 520, an alarm is given, thereby not only visually but also acoustically checking whether the electrical current is reduced.

The configuration described above may be applied when the screw nail body 500 is formed as a tapping screw as shown in FIG. 12, in which it is possible sense nerves while forming a hole for inserting the screw nail body 500, thereby preventing damages in nerves.

Due to this, during a perforating process and an insertion process of the screw nail body 500, nerves may be doubly monitored.

As described above, the medical insertion apparatus 50 according to the fifth embodiment may sense contact with nerves and may prevent damages in nerves while being inserted into the human body, may sense contact with another material including nerves using one circuit formed therein according to the short circuit principal, and may estimate a material in contact with the screw nail body depending on a reduction amount of an electrical current. In addition, it may be checked whether neurological contact is present by sensing an electromyogram using an electrical current transferred to nerves.

Figure 15:
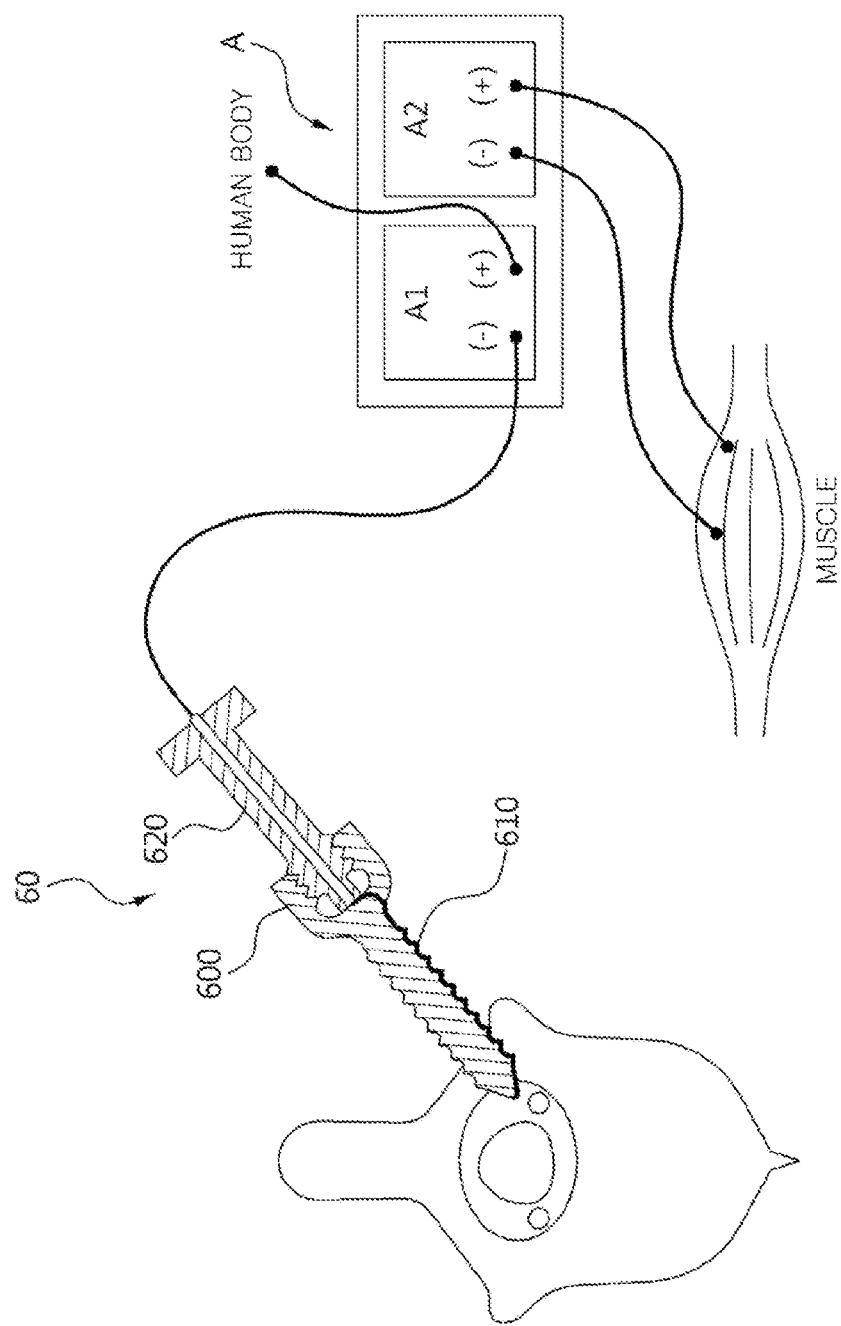
FIG. 15 illustrates a medical insertion apparatus according to a sixth embodiment of the present invention.
Figure 16:
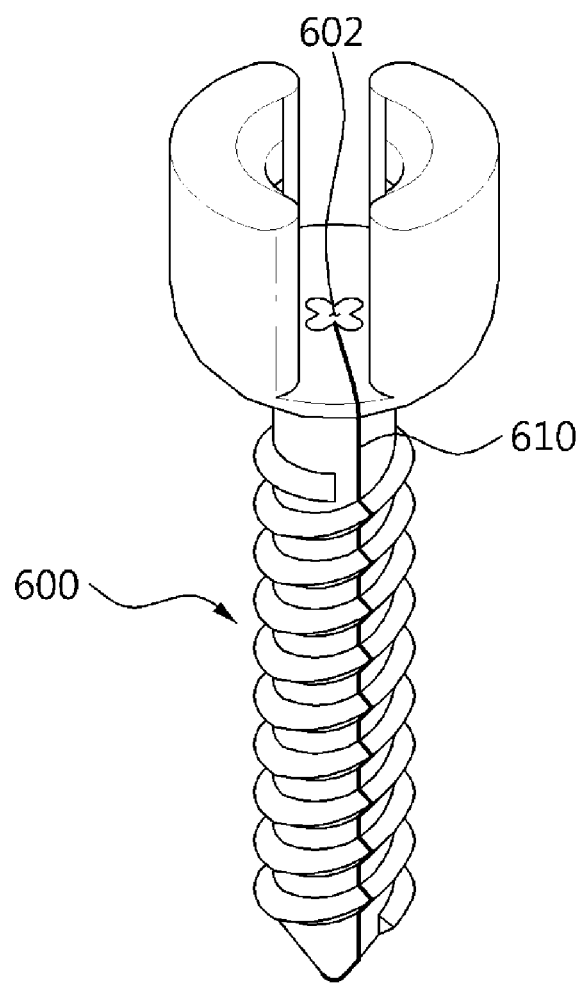
FIG. 16 illustrates a state in which an electrode is coupled with a screw nail body in the medical insertion apparatus according to the sixth embodiment.
Figure 17:
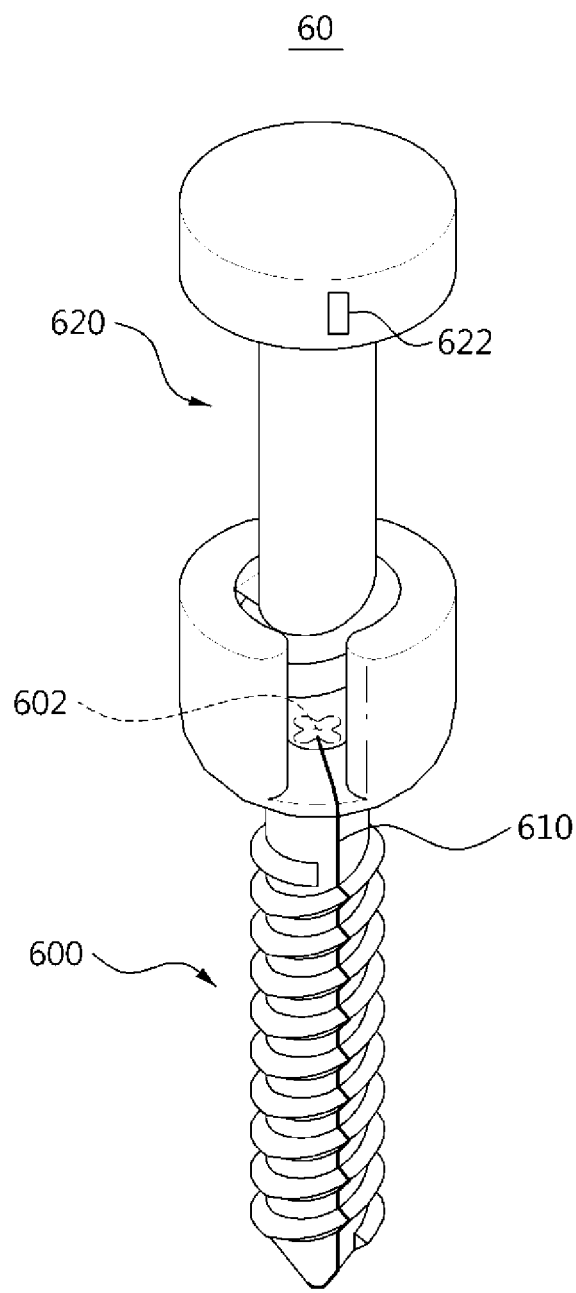
FIG. 17 illustrates a state in which an indicator element is disposed in a driver in the medical insertion apparatus according to the sixth embodiment.
Figure 18:
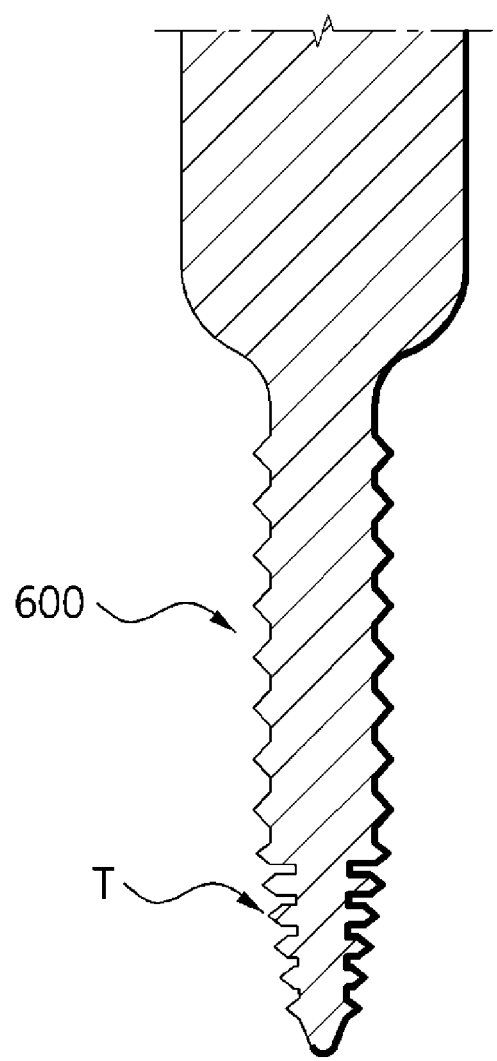
FIG. 18 illustrates a state in which the screw nail body is formed as a tapping screw in the medical insertion apparatus according to the sixth embodiment.
Figure 19A:
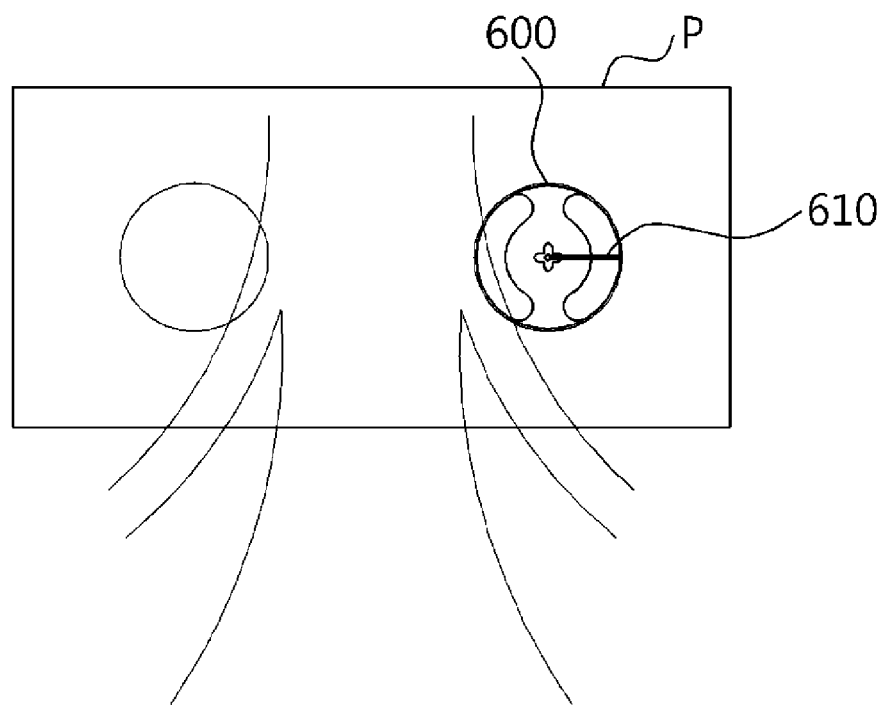
FIGS. 19a and 19b illustrate states in which the medical insertion apparatus according to the sixth embodiment is inserted into a human body.
Figure 19B:
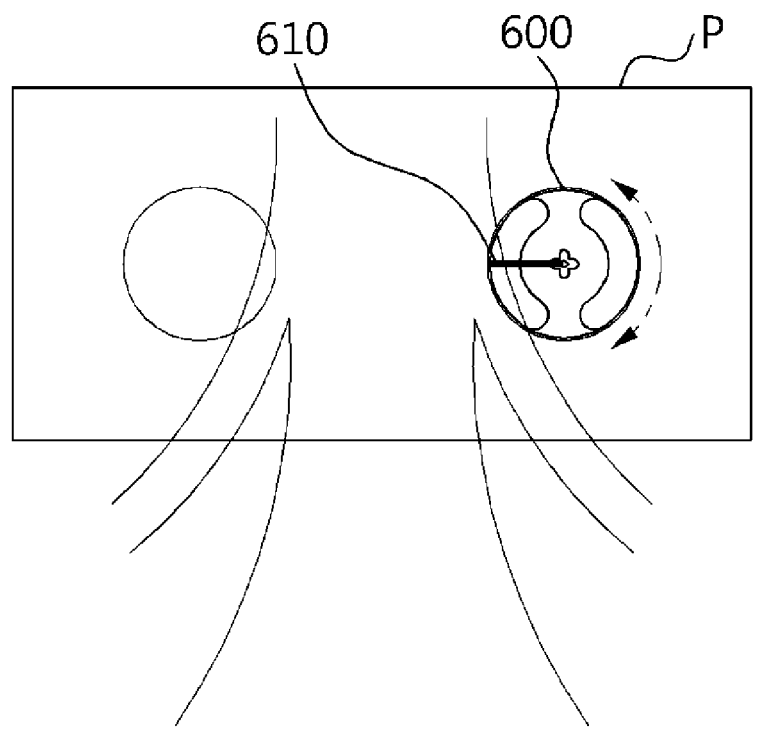

FIG. 15 illustrates a medical insertion apparatus according to a sixth embodiment of the present invention. FIG. 16 illustrates a state in which an electrode is disposed with a screw nail body in the medical insertion apparatus according to the sixth embodiment. FIG. 17 illustrates a state in which an indicator element is disposed in a driver in the medical insertion apparatus according to the sixth embodiment. FIG. 18 illustrates a state in which the screw nail body is formed as a tapping screw in the medical insertion apparatus according to the sixth embodiment. FIGS. 19a and 19b illustrate a state in which the medical insertion apparatus according to the sixth embodiment is inserted into a human body.

Referring to FIG. 15, a medical insertion apparatus 60 according to the sixth embodiment may include a screw nail body 600, an electrode 610, and a driver 620.

The medical insertion apparatus 60 according to the sixth embodiment may be used while being connected with a nerve stimulating and monitoring apparatus A.

The nerve stimulating and monitoring apparatus A may include apparatuses for EMG, EP, MEP, and SSEP.

However, the nerve stimulating and monitoring apparatus A is not limited thereto and may be any one which includes components for electrically stimulating muscles or nerves and receiving or detecting a signal generated by muscles or nerves due to the electrical stimulus.

The nerve stimulating and monitoring apparatus A may include a nerve stimulator A1 and a stimulus receptor A2.

The nerve stimulator A1 is a component which directly applies a micro electrical current to nerves, and the stimulus receptor A2 is a component which detects a signal caused by the electrical current from nerves or muscles.

In detail, the electrode 610 included in the medical insertion apparatus 60 according to the sixth embodiment may form one of electrodes which are directly connected to the nerve stimulator A1 and directly apply a micro electrical current to nerves.

Accordingly, when the electrode 610 of the medical insertion apparatus 60 which is inserted during an operation or treatment is in contact with nerves, an electrical current is applied to nerves and a signal is caused at muscles or nerves. When the caused signal is detected by the stimulus receptor A2, neurological contact of the medical insertion apparatus 60 according to the sixth embodiment may be known.

A detailed structure of the medical insertion apparatus 60 according to the sixth embodiment will be described below.

The screw nail body 600 may be inserted into a human body and may include a screw thread on an outside thereof.

For example, since the screw nail body 600 may be inserted into spine, teeth, or muscles, the screw nail body 600 may be manufactured using titanium which has excellent biocompatibility and strength and is used as a material for various implants.

The electrode 610 may be exposed at an outside of the screw nail body 600.

The electrode 610 may be formed of platinum, gold, silver, tungsten, etc., which are biocompatible with the human body and has excellent electrical conductivity.

For example, the electrode 610 may be formed of platinum attached to the outside of the screw nail body 600 to be exposed. Alternatively, the electrode 610 may be formed by plating the outside of the screw nail body 600 with a conductive material.

As described above, since the electrode 610 may be formed on the screw nail body 600 using a relatively simple method, the electrode 610 may be easily applied an existing screw nail body.

In addition, it is unnecessary to form the electrode 610 in the screw nail body 600, time and cost for manufacturing the screw nail body 600 may be reduced.

In detail, referring to FIG. 16, the electrode 610 may extend from a top end of the screw nail body 600 to an end portion of the screw nail body 600 along a longitudinal direction of the screw nail body 600 and may straightly extend from an outer circumferential surface of the screw nail body 600 along the longitudinal direction of the screw nail body 600.

Here, the electrode 610 may be provided in a piece of string and may extend from the top end of the screw nail body 600 to a center of the end portion of the screw nail body 600 along an outer circumference of the screw nail body 600.

As described above, the electrode 610 may extend in a certain direction on the outer circumference of the screw nail body 600 and may be exposed outward along the longitudinal direction of the screw nail body 600, thereby sensing contact with nerves in all positions along the longitudinal direction of the screw nail body 600.

Accordingly, contact between the screw nail body 600 and nerves may be sensed during the whole process from an initial stage to a complete stage of inserting the medical insertion apparatus 60 according to the sixth embodiment.

When being in contact with the end portion of the screw nail body 600, a nerve slightly slides and steers thereby. Here, since a nerve root may be damaged when proceeding by force, it is necessary to increase a contact area between the electrode 610 and the nerve to prevent the nerve from being damaged. In an aspect described above, it may be preferable that the electrode 610 is exposed at the outside of the screw nail body 600 along the longitudinal direction of the screw nail body 600.

Also, although the electrode 610 is provided in the piece of string, since the screw nail body 600 is inserted into the human body while rotating, the electrode 610 may also rotate together and may sense nerves located in all directions.

However, the number of the electrodes 610 is not limited thereto and a plurality of such electrodes 610 may be formed on the outer circumferential surface of the screw nail body 600 to allow an electrical current to flow through the respective electrodes 610.

The electrode 610 configured as described above may be directly connected to the nerve stimulator A1 but may take a configuration in which the electrode 610 is connected to the nerve stimulator A1 with the driver 620 intervening therebetween to reduce manufacturing costs of the screw nail body 600 and to simplify an operation of processing a wire connected to the nerve stimulator A1 after being inserted into the human body.

For this, the driver 620 may be engaged with a top of the screw nail body 600.

The driver 620 may insert or remove the screw nail body 600 into or from the human body. In detail, the driver 620 may tighten or loosen the screw nail body 600.

For example, two branches which elongate may be formed on the top end of the screw nail body 600 described above and the driver 620 may be inserted between the branches to tighten or loosen the screw nail body 600.

Also, a groove 602 may be formed at the top of the screw nail body 600 and a protrusion may be formed at a bottom of the driver 620 corresponding to a shape of the groove 602.

Alternatively, a protrusion may be formed at the top of the screw nail body 600 and a groove may be formed at the bottom of the driver 620 corresponding to a shape of the protrusion.

As described above, as the screw nail body 600 and the driver 620 rotate while being engaged with each other, the screw nail body 600 may be inserted into and fixed to the human body or may be separated therefrom.

Here, the driver 620 may be electrically connected to the electrode 610 formed on the screw nail body 600.

To make sure electrical contact between the driver 620 and the electrode 610, an end of the driver 620 may be allowed to be inserted into the screw nail body 600.

In detail, since the electrode 610 is connected from the top end of the screw nail body 600 to one side of the groove 602, the electrode 610 and the driver 620 may be electrically connected to each other when the driver 620 is fastened to the groove 602.

Also, the driver 620 may include an indicator element 622.

The indicator element 622 may be any form which allows a direction which the electrode 610 faces to be visually checked.

Referring to FIG. 17, the indicator element 622 may be disposed in the same direction which the electrode 610 faces when the driver 620 is first fastened to the groove 602 of the screw nail body 600.

Accordingly, when the driver 620 is fastened to the screw nail body 600 and rotates, the indicator element 622 included in the driver 620 and the electrode 610 may face the same direction.

The direction which the indicator element 622 faces is checked due to this, thereby knowing the direction which the electrode 610 faces when the screw nail body 600 is inserted into the human body.

Also, since it is possible to know the direction of the electrode 610 when the electrode 610 is in contact with a nerve, a direction in which the nerve is located may also be known. Accordingly, it is possible to minimize damage in the nerve while the screw nail body 600 is inserted into the human body.

The medical insertion apparatus 60 according to the sixth embodiment, configured as described above, may be used as a tool to be used to previously perforate before the screw nail body 600 is inserted into the human body.

Referring to FIG. 18, the screw nail body 600 may be formed as a tapping screw T.

Here, the screw nail body 600 may be more safely inserted into the human body through a hole provided by the tapping screw T.

As described above, when the electrode 610 is disposed on the outer circumference of the screw nail body 600 formed as the tapping screw T, neurological damage which may occur during a perforating process may be prevented.

In detail, the medical insertion apparatus 60 according to the sixth embodiment may be inserted into the human body and may sense nerves as follows.

First, the driver 620 is fastened to the groove 602 at the top end of the screw nail body 600, thereby electrically connecting the driver 620 with the electrode 610 connected to the groove 602.

After that, the driver 620 is rotated to insert the screw nail body 600 into the human body.

Here, as shown in FIGS. 19a and 19b, the electrode 610 formed on one side of the outer circumferential surface of the screw nail body 600 may not be or may be in contact with nerves.

FIGS. 19a and 19b illustrate, for example, a case of inserting the medical insertion apparatus 60 into the human body through a hole formed in a spine-fixing plate P.

In detail, since the electrode 610 is formed on the outside of the screw nail body 600 with certain directivity, when the electrode 610 faces a direction different from a direction in which a nerve is located as shown in FIG. 19a, the electrode 610 may not be in contact with the nerve.

On the contrary, when the electrode 610 faces the same direction as a direction in which the nerve is located as shown in 19b, the electrode 610 may be in contact with the nerve.

For example, when the electrode 610 is in contact with a nerve in a certain direction, since it is possible to know a direction in which the nerve is located, the screw nail body 600 may be inserted to be far from the direction.

Also, when the electrode 610 is in contact with the nerve, an electrical current transferred from the nerve stimulator A1 may be transferred to the nerve. Here, the electrical current which acts on nerves causes a signal at muscles or nerves and the stimulus receptor A2 may detect a caused EMG signal from muscles or nerves.

Accordingly, when the screw nail body 600 is in contact with nerves, an electrical current is applied thereto and a signal is caused at muscles. When the caused signal is detected by the stimulus receptor A2, neurological contact of the screw nail body 600 may be known in real time.

As described above, since the medical insertion apparatus according to the sixth embodiment increases in a surface in contact with nerves, nerves may be efficiently sensed, neurological damage may be prevented, nerves located around may be sensed during the whole insertion process, a direction in which a nerve is located may be known using an electrode formed in a certain direction, and a direction of the electrode while a driver rotates a screw nail body may be known.

Figure 20:
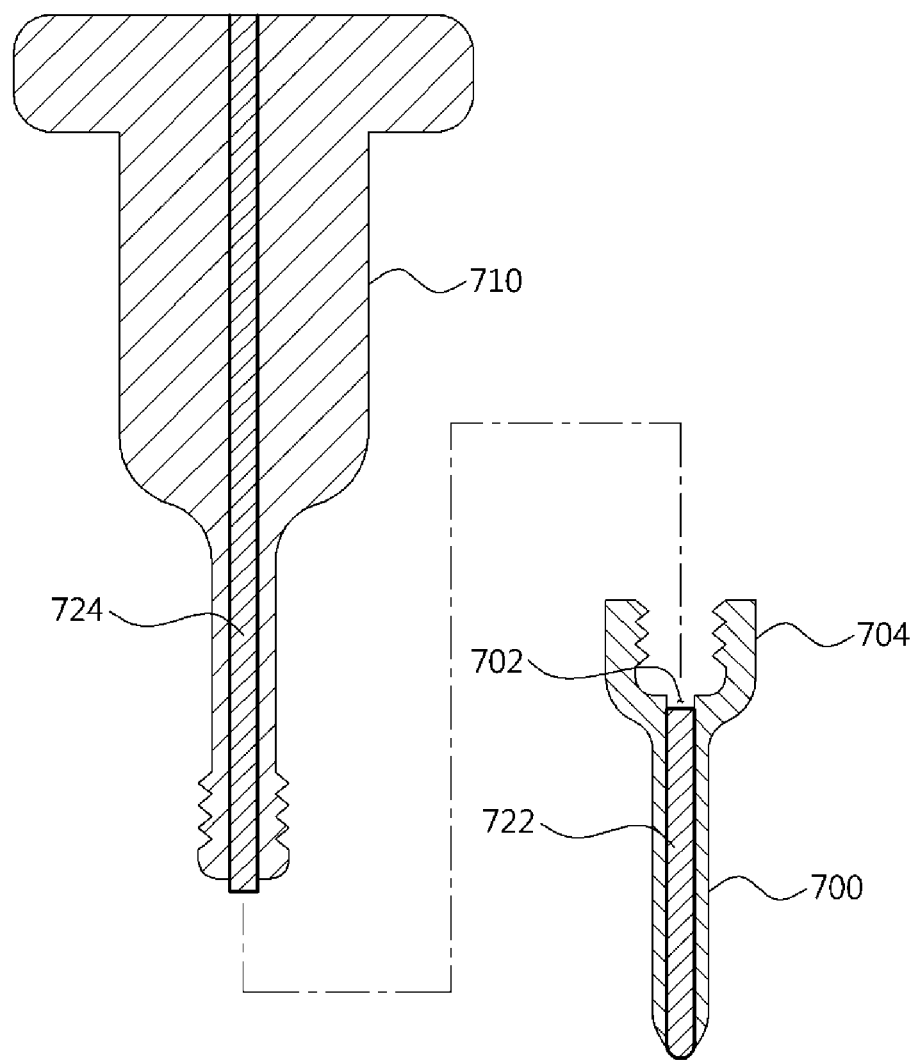
FIG. 20 illustrates a medical insertion apparatus according to a seventh embodiment of the present invention.
Figure 21:
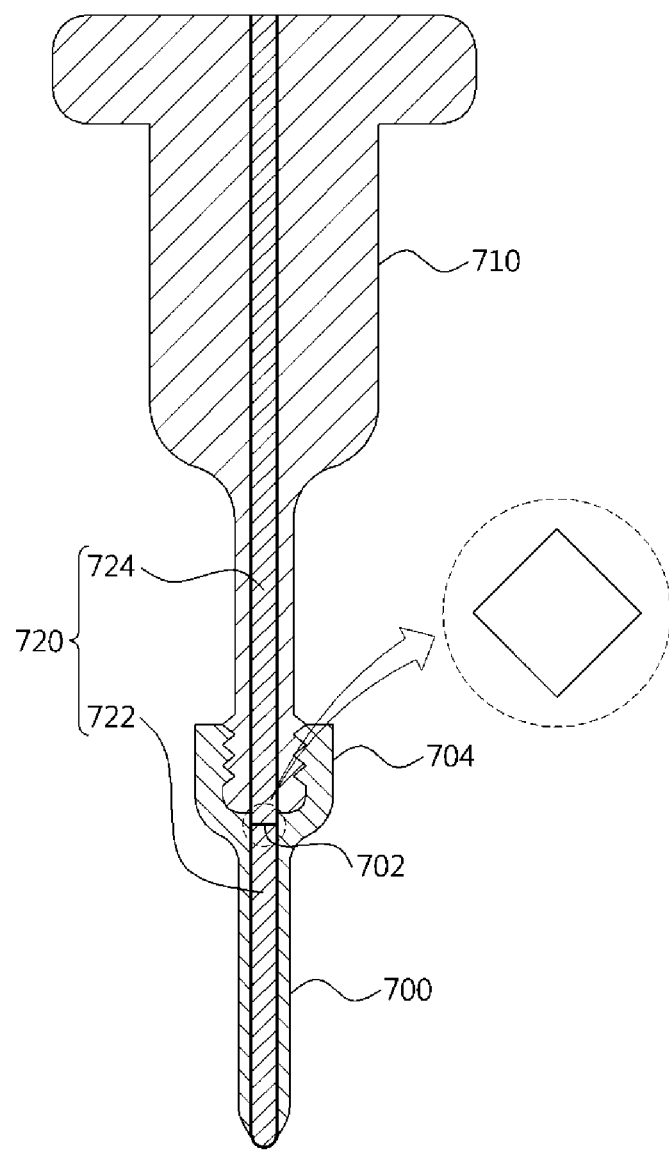
FIG. 21 illustrates a state in which a screw nail body is coupled with a driver in the medical insertion apparatus according to the seventh embodiment.
Figure 22:
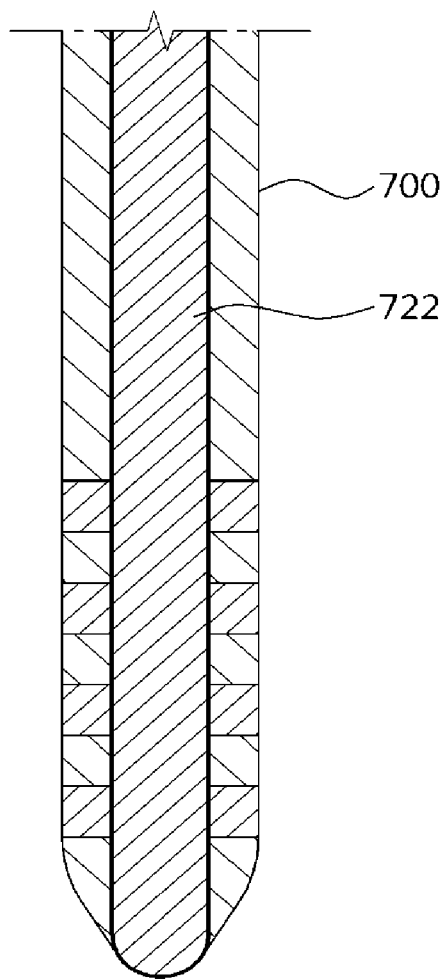
FIG. 22 illustrates a state in which a conductor portion in the medical insertion apparatus according to the seventh embodiment is exposed at a part of the screw nail body.
Figure 23:
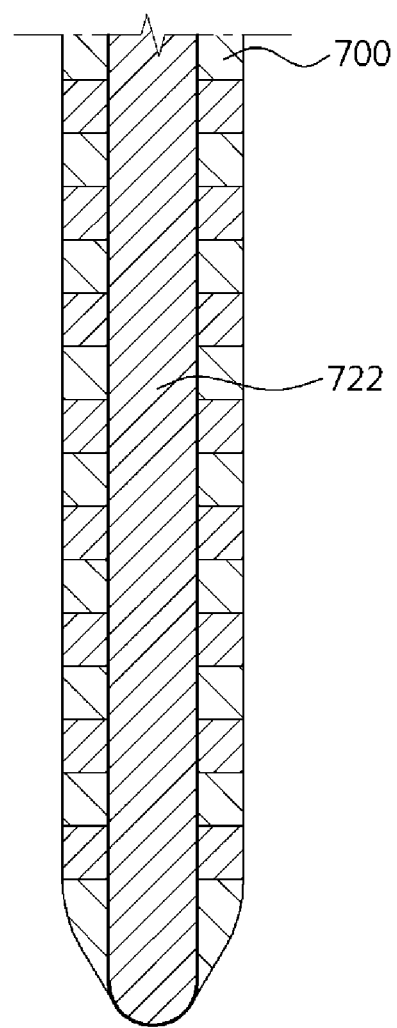
FIG. 23 illustrates a state in which the conductor portion in the medical insertion apparatus according to the seventh embodiment is exposed throughout the whole screw nail body.

FIG. 20 illustrates a medical insertion apparatus according to a seventh embodiment. FIG. 21 illustrates a state in which a screw nail body is coupled with a driver in the medical insertion apparatus according to the seventh embodiment. FIG. 22 illustrates a state in which a conductor portion in the medical insertion apparatus according to the seventh embodiment is exposed at a part of the screw nail body. FIG. 23 illustrates a state in which the conductor portion in the medical insertion apparatus according to the seventh embodiment is exposed at the whole screw nail body.

Referring to FIG. 20, a medical insertion apparatus 70 according to the seventh embodiment may include a screw nail body 700, a driver 710, and a conductor portion 720.

The medical insertion apparatus 70 according to the seventh embodiment may be used while being connected with a nerve stimulating and monitoring apparatus (not shown).

The nerve stimulating and monitoring apparatus may include apparatuses for EMG, EP, MEP, and SSEP.

However, the nerve stimulating and monitoring apparatus is not limited thereto and may be any one which includes components for electrically stimulating muscles or nerves and receiving or detecting a signal generated by muscles or nerves due to the electrical stimulus.

The nerve stimulating and monitoring apparatus may include a nerve stimulator and a stimulus receptor.

The nerve stimulator is a component which directly applies a micro electrical current to nerves, and the stimulus receptor is a component which detects a signal caused by the electrical current from nerves or muscles.

In detail, the electrode 720 included in the medical insertion apparatus 70 according to the seventh embodiment may form one of electrodes which are connected to the nerve stimulator and directly apply a micro electrical current to nerves.

Accordingly, when the electrode 720 of the medical insertion apparatus 70 which is inserted during an operation or treatment is in contact with nerves, an electrical current is applied to nerves and a signal is caused at muscles or nerves. When the caused signal is detected by the stimulus receptor, neurological contact of the medical insertion apparatus 70 according to the seventh embodiment may be known.

A detailed structure of the medical insertion apparatus 70 according to the seventh embodiment will be described below.

The screw nail body 700 may be inserted into a human body and may include a screw thread on an outside thereof.

In detail, the screw nail body 700 may be inserted into spine, teeth, or muscles. For example, the screw nail body 700 may be formed in a synostosis screw nail to be inserted into osseous tissue adjacent to a nerve, and more particularly, may be formed in a pedicle screw to be inserted into spine, etc.

Accordingly, the screw nail body 700 may be manufactured using titanium which has excellent biocompatibility and strength to be used as a material for various implants A groove 702 may be formed at a top end of the screw nail body 700.

An end portion of the driver 710 may be inserted into the groove 702 of the screw nail body 700.

Due to this, a shape of the groove 702 may be provided corresponding to a shape of the end portion of the driver 710.

For example, a cross section of the groove 702 may include a tetragon, a circle, or a hexagon.

Also, a protruding element 704 to be engaged with the driver 710 may be provided at the top end of the screw nail body 700.

In detail, two protruding elements 704 may be provided on the top end of the screw nail body 700 and the driver 710 may be inserted between the two protruding elements 704. Also, the protruding elements 704 may extend from the screw nail body 700 at a length appropriate for the driver 710 to be engaged.

A screw thread may be formed on an inside of the protruding element 704.

The screw thread is to be screw-coupled with the driver 710. Corresponding to the screw thread of the protruding element 704, a screw thread may be formed on an outside of the driver 710.

As described above, due to screw-coupling between the screw thread formed on the protruding element 704 of the screw nail body 700 and the screw thread formed on the outside of the driver 710, tractive force may occur between the screw nail body 700 and the driver 710 and the driver 710 may be mounted on the screw nail body 700.

As described above, the driver 710 may be mounted on the top end of the screw nail body 700.

The driver 710 is to be engaged with the screw nail body 700 to tighten or loosen the screw nail body 700 and may help the screw nail body 700 to be inserted into the human body.

The end portion of the driver 710, as described above, may be formed corresponding to the shape of the groove 702 formed at the top end of the screw nail body 700.

In detail, the end portion of the driver 710 may protrude to be inserted into the groove 702 of the screw nail body 700.

Also, a screw thread may be formed on a side adjacent to the end portion of the driver 710 corresponding to the screw thread of the protruding element 704 of the screw nail body 700.

The conductor portion 720 may be provided in the screw nail body 700 and the driver 710 as described above.

The conductor portion 720 may sense contact with nerves while the screw nail body 700 is inserted into the human body.

The conductor portion 720 may include a first conductor 722 and a second conductor 724.

The first conductor 722 may be disposed in the screw nail body 700.

In detail, a hole (not shown) which penetrates the screw nail body 700 from one end to an end portion thereof may be provided in a center of the screw nail body 700 to dispose the first conductor 722 therein.

Here, the first conductor 722 may be formed by filling the hole with a melted material of electrode and solidifying the material through cooling at a room temperature.

For example, some protrusions or grooves may be formed in an inner circumferential surface of the hole and then the hole is filled with the melted material of electrode and the melted material may be solidified. In this case, the first conductor 722 may be more strongly fixed to the hole, thereby being stably disposed in the screw nail body 700.

Here, the material of the first conductor 722 may be platinum, gold, silver, tungsten, etc. and may be a material which has verified biocompatibility with a human body and excellent electric conductivity to be appropriate for detecting a micro signal.

Here, the first conductor 722 may be exposed outward at the groove 702 formed at the top end of the screw nail body 700 and may be connected to the second conductor 724.

The second conductor 724 may be disposed in the driver 710.

In detail, the second conductor 724 may extend from one end of the driver 710 to the other end of the driver 710 along a longitudinal direction of the driver 710.

Like the first conductor 722, the second conductor 724 may be formed by filling a hole formed in the driver 710 with a melted material of electrode and solidifying the material through cooling at a room temperature.

Here, the second conductor 724 may be exposed outward at the end portion of the driver 710.

Particularly, the second conductor 724 may be exposed at a portion of the driver 710, which is to be inserted into the groove 702 formed at the top end of the screw nail body 700.

Also, the second conductor 724 may be exposed outward in a position of the driver 710 connected to the nerve stimulating and monitoring apparatus.

Referring to FIG. 21, when the screw nail body 700 and the driver 710 are coupled with each other, the first conductor 722 and the second conductor 724 may be electrically connected as follows.

In detail, when the screw thread formed on the protruding element 704 of the screw nail body 700 and the screw thread formed on the driver 710 are screw-coupled, a force of the driver 710 to push the screw nail body 700 may occur and the end portion of the driver 710 may be in contact with the groove 702 formed at the top end of the screw nail body 700 due to the force.

Here, the first conductor 722 included in the screw nail body 700 may be exposed outward at the groove 702. Also, the second conductor 724 included in the driver 710 may be exposed outward at the end portion of the driver 710 inserted into the groove 702. Due to this, the first conductor 722 and the second conductor 724 may be in contact with each other.

Particularly, since the cross section of the groove 702 is provided as a circle, tetragon, or hexagon, the first conductor 722 and the second conductor 724 may be in surface contact with each other.

As described above, electrical connection caused by the surface contact between the first conductor 722 and the second conductor 724 may increase a contact rate between the first conductor 722 and the second conductor 724 while preventing a friction phenomenon between the first conductor 722 and the second conductor 724.

In addition, more various metals may be used to manufacture the conductor portion 720.

In detail, the first conductor 722 may be formed of a metal with lower sensitivity such as platinum, tungsten, etc. described above and the second conductor 724 may be formed of a metal with excellent conductivity and strength such as tungsten in addition to platinum.

Also, the conductor portion 720, particularly, the first conductor 722 may be exposed outward in various positions of the screw nail body 700.

First, as shown in FIGS. 20 and 21, the first conductor 722 may be exposed outward at the end portion of the screw nail body 700.

Here, since the first conductor 722 is exposed only at the end portion of the screw nail body 700, the medical insertion apparatus 70 according to the seventh embodiment may be relatively easily molded while being manufactured.

Also, since the first conductor 722 is exposed at a portion which is the first one to be in contact with a nerve, the nerve may be initially sensed when the medical insertion apparatus 70 according to the seventh embodiment is inserted into the human body.

Referring to FIG. 22, the first conductor 722 may be exposed outward at a point spaced apart from the end portion of the screw nail body 700.

In detail, the first conductor 722 may be exposed outward half an outer circumference of the screw nail body 700.

Here, the first conductor 722 may vertically or slantly extend from the center of the screw nail body 700 toward the outer circumference of the screw nail body 700.

Referring to FIG. 23, the first conductor 722 may be exposed outward at the whole outer circumference of the screw nail body 700.

Although not shown in the drawings in detail, an externally exposed portion of the first conductor 722 may be provided as an annular shape.

Due to the conductor portion 720 configured as described above, the medical insertion apparatus 70 according to the seventh embodiment may monitor nerves in various aspects with respect to the screw nail body 700, thereby extending a range of monitoring nerves.

In detail, contact with nerves may be sensed by the medical insertion apparatus 70 according to the seventh embodiment as follows.

First, the driver 710 and the screw nail body 700 are screw-coupled.

In detail, the screw thread formed on the driver 710 and the screw thread formed on the protruding element 704 of the screw nail body 700 may be screw-coupled with each other.

Here, the end portion of the driver 710 is inserted into the groove 702 formed on the top end of the screw nail body 700.

Due to this, the first conductor 722 and the second conductor 724 may be in surface contact with each other.

After that, electrical stimulus is transferred from the nerve stimulating and monitoring apparatus to the second conductor 724 of the driver 710.

When the electrical stimulus is transferred to the second conductor 724, the electrical stimulus is transferred to the first conductor 722 electrically connected to the second conductor 724.

For example, when the screw nail body 700 is in contact with a nerve, electrical stimulus is transferred to the nerve by the first conductor 722 exposed outward at the screw nail body 700.

The electrical stimulus transferred to the nerve as described above is sensed again by the nerve stimulating and monitoring apparatus.

As described above, in the case of the medical insertion apparatus 70 according to the seventh embodiment, the contact rate of the conductor portion may be increase using tractive force between the screw nail body and the driver, the friction phenomenon of the conductor portion caused by surface contact of the conductor portion may prevented, the conductor portion may be manufactured using various metals, and nerves may be efficiently sensed and may be prevented from being damaged by increasing a contact area with nerves.

Figure 24:
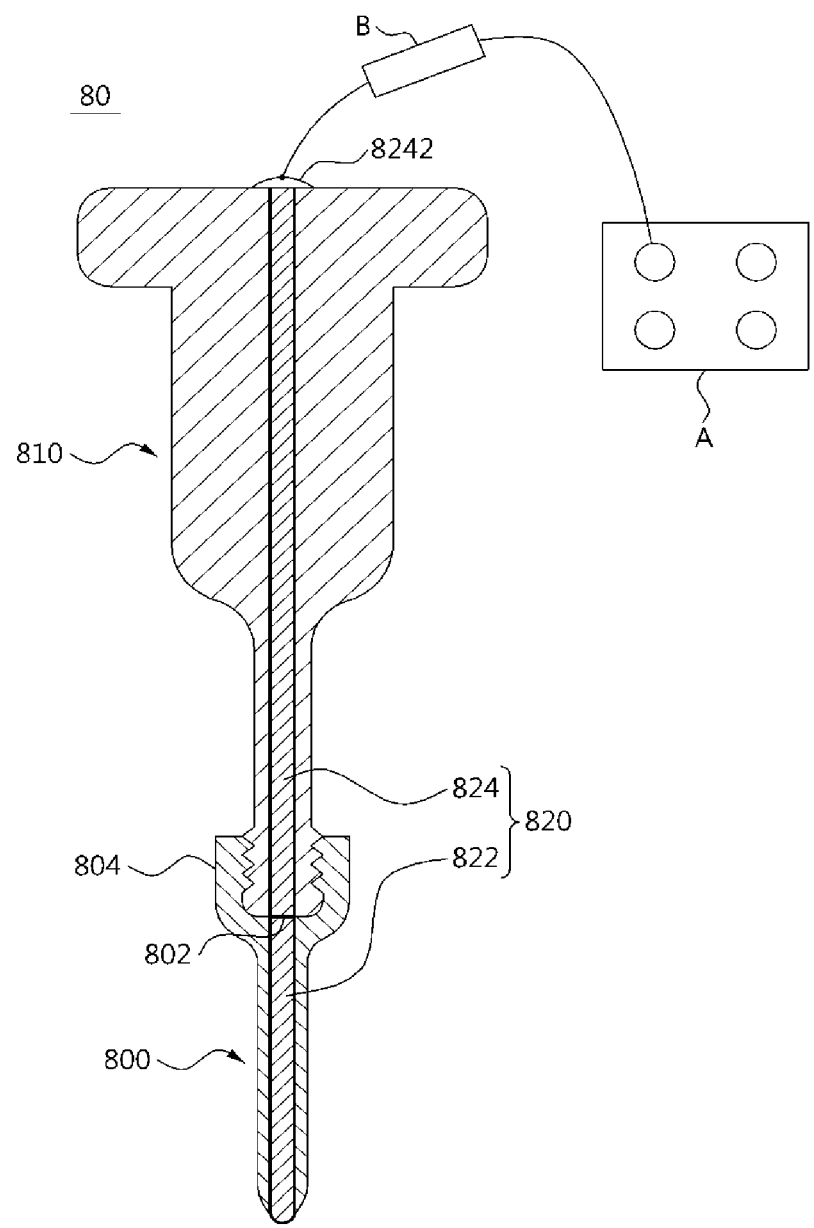
FIG. 24 illustrates a medical insertion apparatus according to an eighth embodiment of the present invention.
Figure 25:
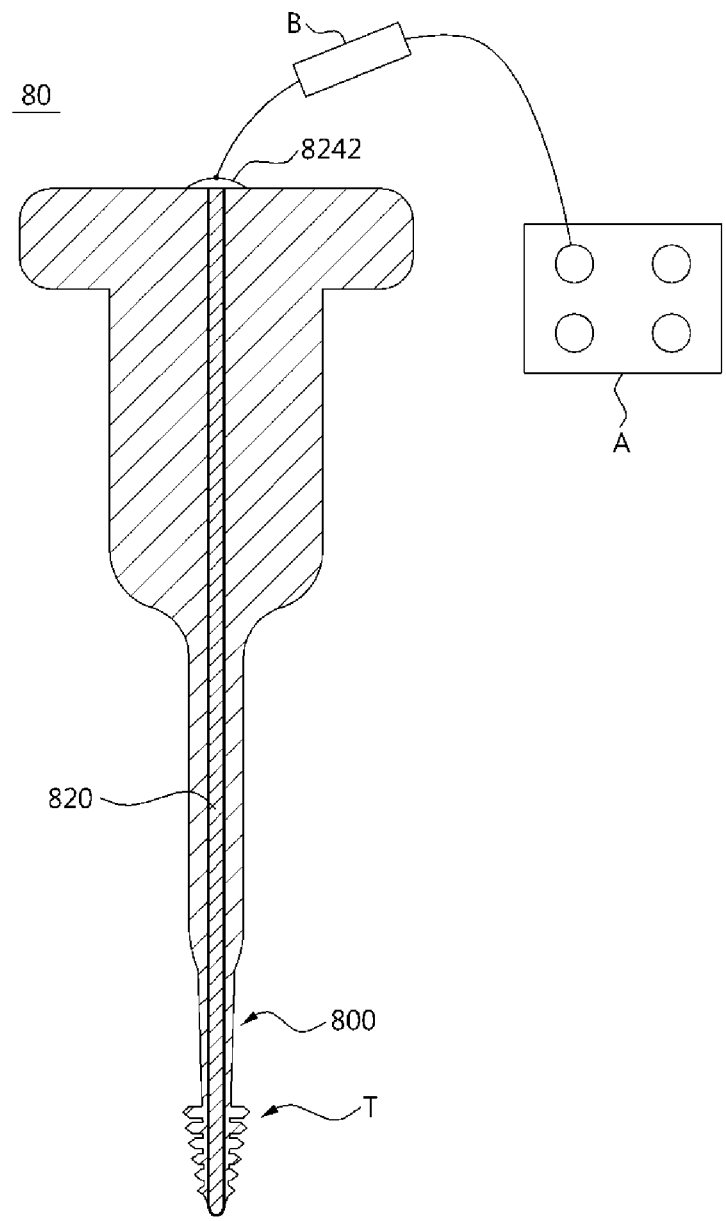
FIG. 25 illustrates a state in which a screw nail body is formed as a tapping screw in the medical insertion apparatus according to the eighth embodiment.

FIG. 24 illustrates a medical insertion apparatus according to an eighth embodiment of the present invention. FIG. 25 illustrates a state in which a screw nail body is formed as a tapping screw in the medical insertion apparatus according to the eighth embodiment of the present invention.

The medical insertion apparatus 80 according to the eighth embodiment may be used while being connected with a nerve stimulating and monitoring apparatus A.

The nerve stimulating and monitoring apparatus A may include a nerve stimulator and a stimulus receptor.

The nerve stimulator is a component which directly applies a micro electrical current to nerves, and the stimulus receptor is a component which detects a signal caused by the electrical current from nerves or muscles.

Accordingly, when a conductor portion 820 of the medical insertion apparatus 80 which is inserted during an operation or treatment is in contact with nerves, an electrical current is applied to nerves and a signal is caused at muscles or nerves. When the caused signal is detected by the stimulus receptor, neurological contact of the medical insertion apparatus 80 according to the eighth embodiment may be known.

The medical insertion apparatus 80 according to eighth embodiment may be connected to the nerve stimulating and monitoring apparatus A described above with or without wires. A structure of the medical insertion apparatus 80 according to the eighth embodiment will be described below in detail.

Referring to FIG. 24, the medical insertion apparatus 80 according to the eighth embodiment may include a screw nail body 800, a driver 810, and a conductor portion 820.

The screw nail body 800 may be inserted into a human body and may include a screw thread on an outside thereof.

In detail, the screw nail body 800 may be inserted into spine, teeth, or muscles. For example, the screw nail body 800 may be formed in a synostosis screw nail to be inserted into osseous tissue adjacent to a nerve, and more particularly, may be formed in a pedicle screw to be inserted into spine, etc.

Accordingly, the screw nail body 800 may be manufactured using titanium which has excellent biocompatibility and strength to be used as a material for various implants.

A groove 802 may be formed at a top end of the screw nail body 800.

An end of the driver 810 may be inserted into the groove 802 of the screw nail body 800.

Due to this, a shape of the groove 802 may be provided corresponding to a shape of the end of the driver 810.

For example, a cross section of the groove 802 may include a tetragon, a circle, or a hexagon.

Also, a protruding element 804 to be engaged with the driver 810 may be provided at the top end of the screw nail body 800.

In detail, two protruding elements 804 may be provided on the top end of the screw nail body 800 and the driver 810 may be inserted between the two protruding elements 804. Also, the protruding elements 804 may extend from the screw nail body 800 at a length appropriate for the driver 810 to be engaged.

A screw thread may be formed on an inside of the protruding element 804.

The screw thread is to be screw-coupled with the driver 810. Corresponding to the screw thread of the protruding element 804, a screw thread may be formed on an outside of the driver 810.

As described above, due to screw-coupling between the screw thread formed on the protruding element 804 of the screw nail body 800 and the screw thread formed on the outside of the driver 810, tractive force may occur between the screw nail body 800 and the driver 810 and the driver 810 may be mounted on the screw nail body 800.

As described above, the driver 810 may be mounted on the top end of the screw nail body 800.

The driver 810 is to be engaged with the screw nail body 800 to tighten or loosen the screw nail body 800 and may help the screw nail body 800 to be inserted into the human body.

An end portion of the driver 810 may be formed corresponding to the shape of the groove 802 formed at the top end of the screw nail body 800 as described above.

In detail, the end portion of the driver 810 may protrude to be inserted into the groove 802 of the screw nail body 800.

Also, a screw thread may be formed on a side adjacent to the end portion of the driver 810 corresponding to the screw thread of the protruding element 804 of the screw nail body 800.

Referring to FIG. 25, the screw nail body 800 may be formed as a tapping screw T.

The tapping screw T may be used when a perforating process is previously performed before the screw nail body 800 is inserted into the human body.

Here, the screw nail body 800 may be more safely inserted into a hole provided by the tapping screw T.

In detail, when the screw nail body 800 is formed as the tapping screw T, the screw nail body 800 and the driver 810 may be integrally formed.

Also, the conductor portion 820 is formed to be exposed outward on a side where the tapping screw T is formed, contact between the screw nail body 800 and nerves may be sensed during the perforating process.

The conductor portion 820 may be provided in the screw nail body 800 and the driver 810 as described above.

The conductor portion 820 may sense contact with nerves while the screw nail body 800 is inserted into the human body.

The conductor portion 820 may include a first conductor 822 and a second conductor 824.

The first conductor 822 may be disposed in the screw nail body 800.

In detail, a hole (not shown) which penetrates the screw nail body 800 from one end to an end portion thereof may be provided in a center of the screw nail body 800 to allow the first conductor 822 to be disposed therein.

Here, the first conductor 822 may be formed by filling the hole with a melted material of electrode and solidifying the material through cooling at a room temperature.

For example, some protrusions or grooves may be formed in an inner circumferential surface of the hole and then the hole is filled with the melted material of electrode and the melted material may be solidified. In this case, the first conductor 822 may be more strongly fixed to the hole, thereby being stably disposed in the screw nail body 800.

Here, the material of the first conductor 822 may be platinum, gold, silver, tungsten, etc. and may be a material which has verified biocompatibility with a human body and excellent electric conductivity to be appropriate for detecting a micro signal.

Here, the first conductor 822 may be exposed outward at the groove 802 formed at the top end of the screw nail body 800 and may be connected to the second conductor 824.

The second conductor 824 may be disposed in the driver 810.

In detail, the second conductor 824 may extend from one end of the driver 810 to the other end of the driver 810 along a longitudinal direction of the driver 810.

Like the first conductor 822, the second conductor 824 may be formed by filling a hole formed in the driver 810 with a melted material of electrode and solidifying the material through cooling at a room temperature.

Here, the second conductor 824 may be exposed outward at the end portion of the driver 810.

Particularly, the second conductor 824 may be exposed at a portion of the driver 810, which is to be inserted into the groove 802 formed at the top end of the screw nail body 800. This is to be electrically connected to the first conductor 822.

In addition, the second conductor 824 may include an exposure terminal 8242 at the end portion of the driver 810.

The exposure terminal 8242 is a portion of the second conductor 824 exposed outward to be connected to the nerve stimulating and monitoring apparatus A with wires.

Accordingly, the exposure terminal 8242 may be exposed outward in a position of the driver 810 connected to the nerve stimulating and monitoring apparatus A.

The exposure terminal 8242 is provided at the end portion of the driver 810 in FIG. 24 but is not limited thereto and may be provided on a side of the driver 810.

When the screw nail body 800 and the driver 810 are coupled with each other, the first conductor 822 and the second conductor 824 may be electrically connected to each other.

In detail, when the screw thread formed on the protruding element 804 of the screw nail body 800 and the screw thread formed on the driver 810 are screw-coupled, a force of the driver 810 to push the screw nail body 800 may occur and the end portion of the driver 810 may be in contact with the groove 802 formed at the top end of the screw nail body 800 due to the force.

Here, the first conductor 822 included in the screw nail body 800 may be exposed outward at the groove 802. Also, the second conductor 824 included in the driver 810 may be exposed outward at the end portion of the driver 810 inserted into the groove 802. Due to this, the first conductor 822 and the second conductor 824 may be in contact with each other.

Particularly, since the cross section of the groove 802 is provided as a circle, tetragon, or hexagon, the first conductor 822 and the second conductor 824 may be in surface contact with each other.

As described above, electrical connection caused by the surface contact between the first conductor 822 and the second conductor 824 may increase a contact rate between the first conductor 822 and the second conductor 824 while preventing a friction phenomenon between the first conductor 822 and the second conductor 824.

Also, the conductor portion 820, particularly, the first conductor 822 may be exposed outward in various positions of the screw nail body 800.

For example, the first conductor 822 may be exposed outward at the end portion of the screw nail body 800.

In detail, the first conductor 822 may extend from one end of the screw nail body 800 toward an end portion of the screw nail body 800 along a longitudinal direction of the screw nail body 800.

Here, since the first conductor 822 is exposed only at the end portion of the screw nail body 800, the medical insertion apparatus 80 according to the eighth embodiment may be relatively easily molded while being manufactured.

Also, since the first conductor 822 is exposed at a portion which is the first one to be in contact with a nerve, the nerve may be initially sensed when the medical insertion apparatus 80 according to the eighth embodiment is inserted into the human body.

Also, the first conductor 822 may be exposed outward at a point spaced apart from the end portion of the screw nail body 800.

In detail, the first conductor 822 may be exposed outward half an outer circumference of the screw nail body 800.

Here, the first conductor 822 may vertically or slantly extend from the center of the screw nail body 800 toward the outer circumference of the screw nail body 800.

Alternatively, the first conductor 822 may be exposed outward the whole outer circumference of the screw nail body 800.

Although not shown in the drawings in detail, an externally exposed portion of the first conductor 822 may be provided as an annular shape.

Due to the conductor portion 820 configured as described above, the medical insertion apparatus 80 according to the eighth embodiment may monitor nerves in various aspects with respect to the screw nail body 800, thereby extending a range of monitoring nerves.

In detail, contact with nerves may be sensed by the medical insertion apparatus 80 according to the eighth embodiment as follows.

First, the driver 810 and the screw nail body 800 are screw-coupled.

In detail, the screw thread formed on the driver 810 and the screw thread formed on the protruding element 804 of the screw nail body 800 may be screw-coupled with each other.

Here, the end portion of the driver 810 is inserted into the groove 802 formed on the top end of the screw nail body 800.

Due to this, the first conductor 822 and the second conductor 824 may be in surface contact with each other.

After that, electrical stimulus is transferred from the nerve stimulating and monitoring apparatus A to the second conductor 824 of the driver 810.

In detail, a trigger device B may be connected to the nerve stimulating and monitoring apparatus A.

The trigger device B indicates a device which automatically initiates an operation of an electronic circuit, a machine, or a program used to provide a certain stable state and may transfer the electrical stimulus generated at the nerve stimulating and monitoring apparatus A to the second conductor 824.

Particularly, the driver 810 includes the exposure terminal 8242 and an end portion of the trigger device B is in contact with the exposure terminal 8242, thereby easily transferring the electric stimulus from the nerve stimulating and monitoring apparatus A to the conductor portion 820.

When the electrical stimulus is transferred to the second conductor 824, the electrical stimulus is transferred to the first conductor 822 electrically connected to the second conductor 824.

For example, when the screw nail body 800 is in contact with a nerve, electrical stimulus is transferred to the nerve by the first conductor 822 exposed outward at the screw nail body 800.

As described above, the electrical stimulus transferred to the nerve as described above is sensed again by the nerve stimulating and monitoring apparatus A.

As described above, the medical insertion apparatus 80 to the eighth embodiment may increase stability of operation, may reduce a radiation exposure time during an operation, and may be compatible with an existing nerve stimulating and monitoring apparatus without an additional device. In addition, an exposure terminal may be provided to easily connect a conductor portion with a nerve stimulating and monitoring apparatus.

Hereinafter, a medical insertion apparatus 90 according to a ninth embodiment of the present invention, capable of being wirelessly connected with a nerve stimulating and monitoring apparatus will be described. A description of a structure substantially identical or similar to the medical insertion apparatus 80 according to the eighth embodiment will be omitted.

Figure 26:
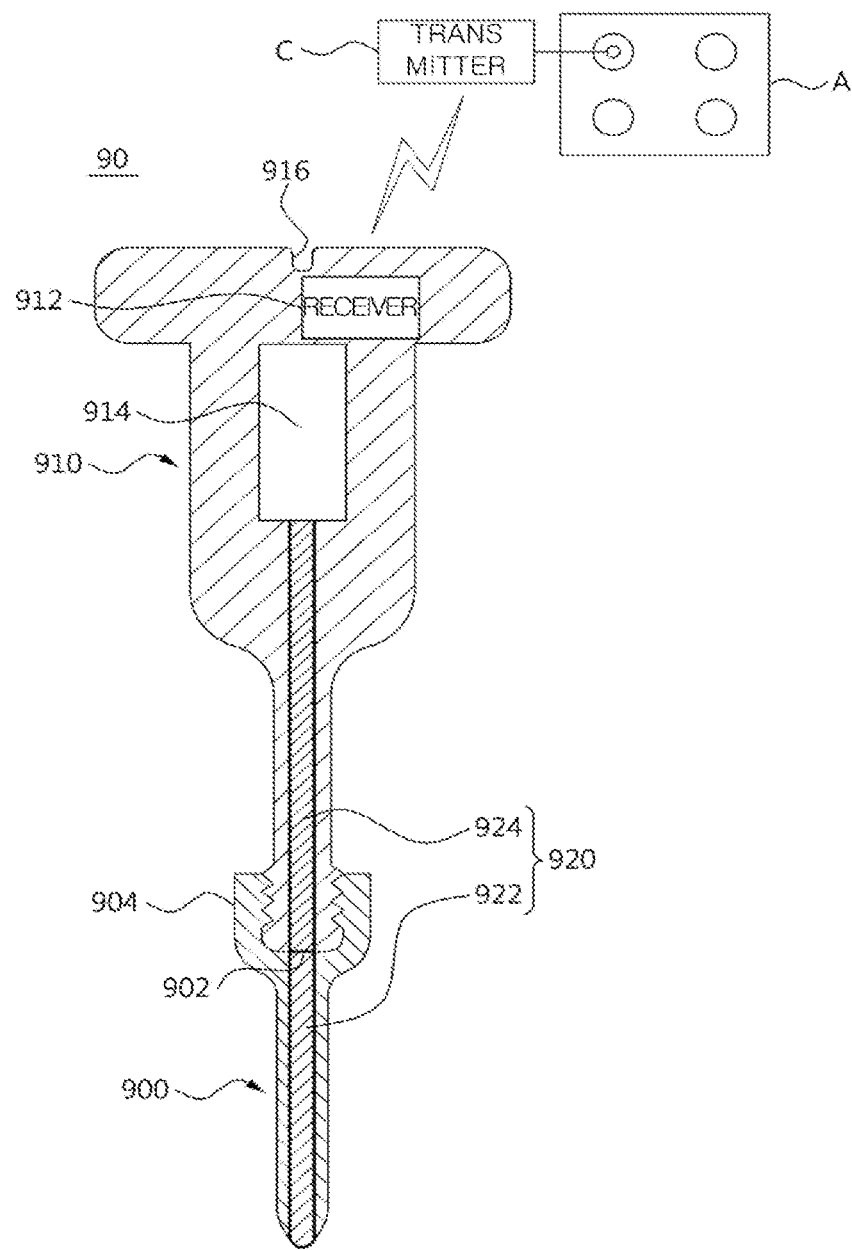
FIG. 26 illustrates a medical insertion apparatus according to a ninth embodiment of the present invention.
Figure 27:
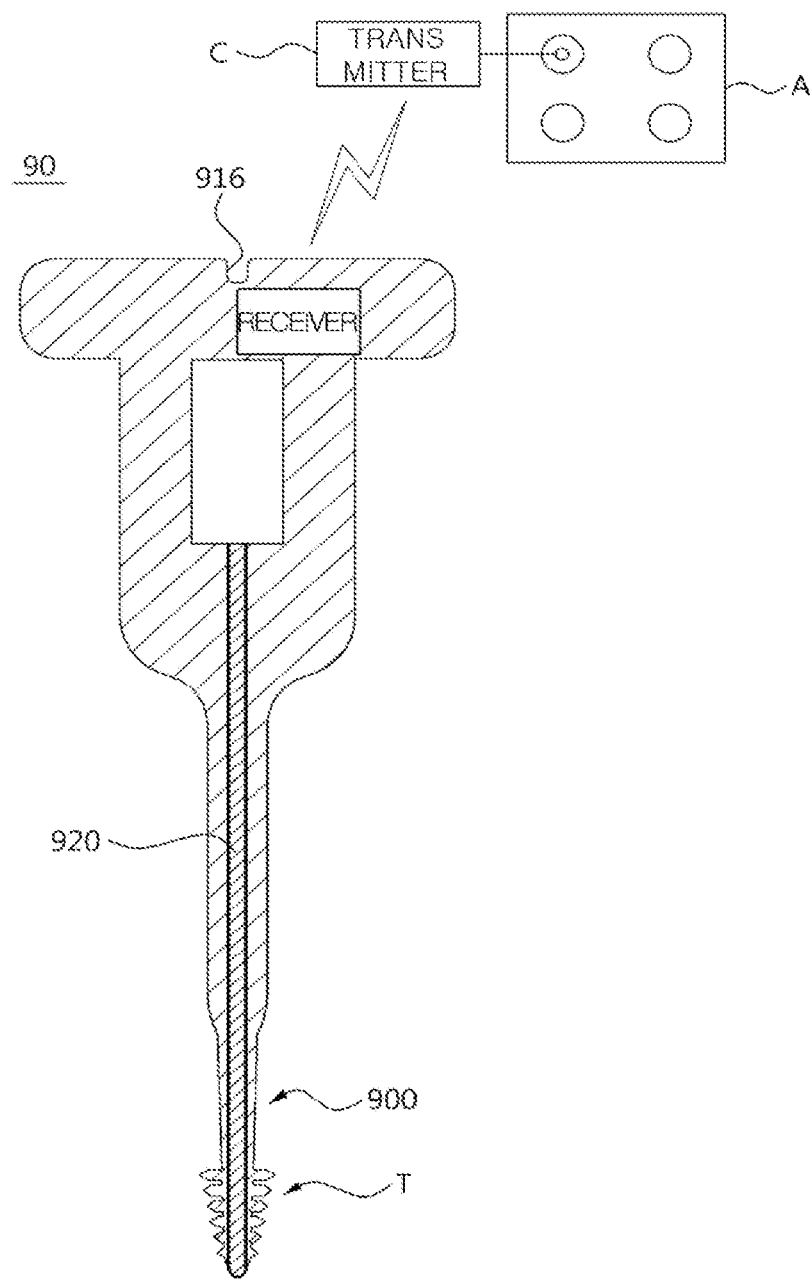
FIG. 27 illustrates a state in which the screw nail body is formed as a tapping screw in the medical insertion apparatus according to the ninth embodiment.
Figure 28:
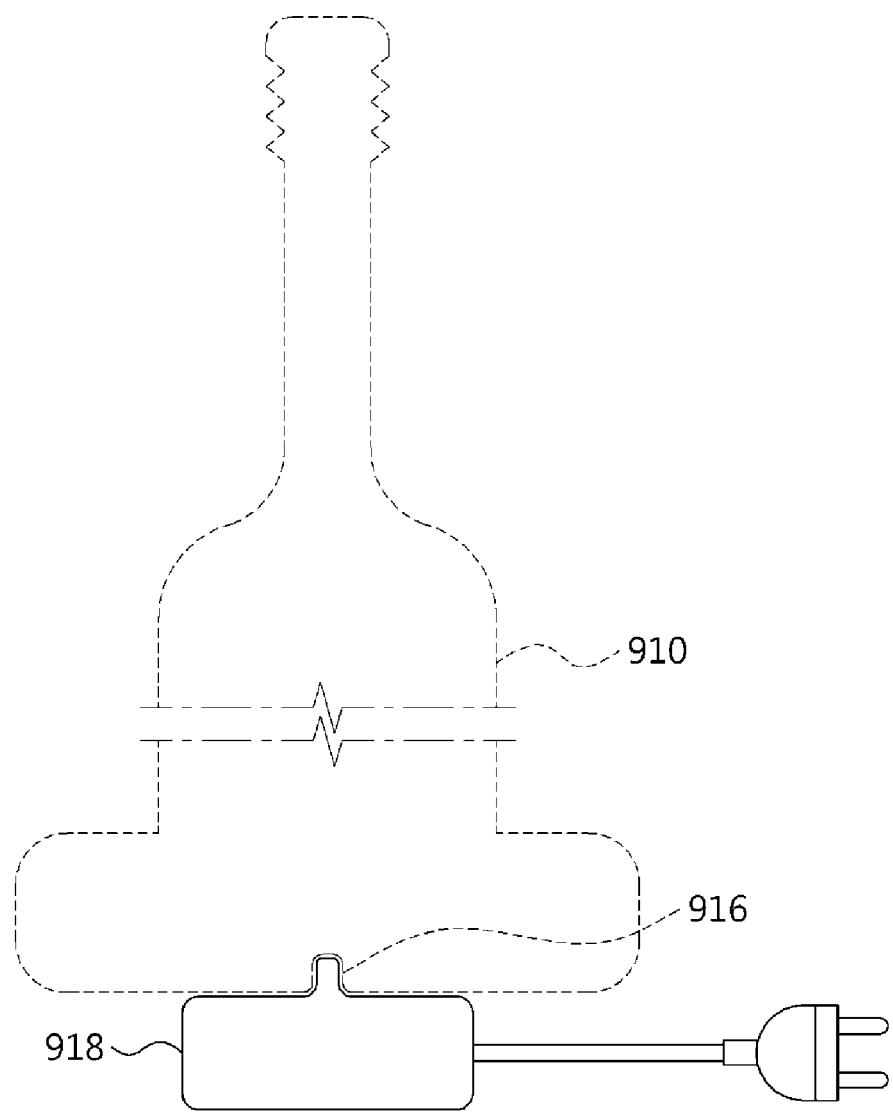
FIG. 28 illustrates a state in which a driver is charged in the medical insertion apparatus according to the ninth embodiment.

FIG. 26 illustrates a medical insertion apparatus according to a ninth embodiment. FIG. 27 illustrates a state in which a screw nail body is formed as a tapping screw in the medical insertion apparatus according to the ninth embodiment. FIG. 28 illustrates a state in which a driver is charged in the medical insertion apparatus according to the ninth embodiment of the present invention.

Referring to FIG. 26, the medical insertion apparatus 90 according to the ninth embodiment may include a screw nail body 900, a driver 910, and a conductor portion 920.

The medical insertion apparatus 90 according to the ninth embodiment may be wirelessly connected to a nerve stimulating and monitoring apparatus, which is a difference from the medical insertion apparatus 80 according to the eighth embodiment.

In detail, the driver 910 may include a receiver 912 and a nerve stimulating and monitoring apparatus A may include a transmitter C.

Electrical stimulus generated from the nerve stimulating and monitoring apparatus A may be wirelessly transmitted from the transmitter C to the receiver 912 of the driver 910.

Also, the driver 910 may include a built-in battery 914.

A second conductor 924 may be connected to the built-in battery 914.

In detail, in the driver 910, the second conductor 924 may extend from the built-in battery 914 to an end portion of the driver 910 to be engaged with the screw nail body 900 along a longitudinal direction of the driver 910.

Also, to charge the built-in battery 914, a charging socket 916 may be mounted on the end portion of the driver 910.

Referring to FIG. 27, when the screw nail body 900 is formed as a tapping screw T, the screw nail body 900 and the driver 910 may be integrally formed.

Including the receiver 912, when a perforating process is previously performed before the screw nail body 900 is inserted into a human body, contact between the screw nail body 900 and a nerve may be wirelessly sensed.

Also, including the built-in battery 914 and the charging socket 916 in one end, it is possible to charge to be used as necessary.

Referring to FIG. 28, the charging socket 916 may be mounted on a charging station 918.

The charging station 918 may be provided in a shape corresponding to a shape of the charging socket 916.

When the charging socket 916 is mounted on the charging station 918 and an electrical plug connected to the charging station 918 is inserted into an electrical outlet, the built-in battery 914 in the driver 910 may be charged.

The medical insertion apparatus 90 according to the ninth embodiment may wirelessly monitor nerves and reduce inconvenience of an operator caused by wires by including the receiver in the driver and may easily charge the built-in battery in the driver, mounted on the charging station.

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

Included in the detailed description.

The invention claimed is:

1. A screw assembly capable of being inserted into a human body comprising:
   a body having a through hole therein, wherein the through hole has a first end and a second end; and
   an electrode having:
      a first portion extending in a longitudinal direction and capable of being inserted into the through hole, and
      a second portion having a rounded conical shape with a circular base, the circular base connected to the first portion, the second portion exposed outward at the second end of the through hole,
   wherein a diameter of the circular base of the second portion is greater than a diameter of the through hole and the circular base of the second portion maintains the second portion as being exposed outward at the second end of the through hole, and
   wherein, when the first portion is inserted in the through hole, a distal end of the first portion is located at the same height of the first end of the through hole.

2. The screw assembly of claim 1, wherein the through hole extends along a longitudinal direction of the body.

3. The screw assembly of claim 1, wherein a through hole screw thread is defined at a surface adjacent to the second end of the through hole, and one end portion of the first portion of the electrode has a screw thread, and when the electrode is inserted into the body, the screw thread of the electrode is located corresponding to a location of the through hole screw thread.

4. A screw assembly capable of being inserted into a human body comprising:
   a body having a through hole which is elongated and has a first end and a second end; and
   an electrode having:
      a first portion extending in a longitudinal direction and capable of being inserted into the through hole, and
      a second portion having a rounded conical shape with a circular base, the circular base adjacent to the first portion, the second portion exposed outward at the second end of the through hole,
   wherein the electrode is detachably attached through the second end of the through hole a diameter of the circular base of the second portion is greater than a diameter of the through hole and the circular base of the second portion maintains the second portion as being exposed outward at the second end of the through hole, and
   wherein, when the first portion is inserted in the through hole, a distal end of the first portion is located at the same height of the first end of the through hole.

5. The screw assembly of claim 4, wherein the electrode is capable of being inserted through the second end of the through hole and is screw-coupled with the through hole.

6. The screw assembly of claim 5, wherein the first portion has a screw thread.

7. The screw assembly of claim 6, wherein the through hole has a through hole screw thread corresponding to the screw thread of the first portion.

8. The screw assembly of claim 7, wherein the screw thread of the first portion and the through hole screw thread are positioned adjacent to the second end of the through hole when the electrode is inserted into the through hole.

9. The screw assembly of claim 4, wherein when the first portion is screw-coupled with the through hole, the distal end of the first portion is located at the same height of the first end of the through hole.

10. The screw assembly of claim 1, wherein a first end portion of the through hole has a non-threaded surface and a second end portion of the through hole has a threaded surface, and wherein one end portion of the first portion of the electrode has a threaded surface and a distal end portion of the first portion of the electrode has a non-threaded surface.

11. The screw assembly of claim 4, wherein a first end portion of the through hole has a non-threaded surface and a second end portion of the through hole has a threaded surface, and wherein one end portion of the first portion of the electrode has a threaded surface and a distal end portion of the first portion of the electrode has a non-threaded surface.

12. The screw assembly of claim 1, wherein the body has a screw head on a side having the first end of the through hole.

13. The screw assembly of claim 4, wherein the body has a screw head on a side having the first end of the through hole.

14. A screw assembly capable of being inserted into a human body comprising:
   a body having a through hole therein, wherein the through hole has a first end and a second end; and
   an electrode having:
      a first portion extending in a longitudinal direction and capable of being inserted into the through hole, and
      a second portion having a rounded conical shape with a circular base, the circular base connected to one end portion of the first portion, the second portion exposed outward at the second end of the through hole, wherein a first end portion of the through hole has a non-threaded surface and a second end portion of the through hole has a threaded surface, and wherein the one end portion of the first portion of the electrode has a threaded surface and a distal end portion of the first portion of the electrode has a non-threaded surface, wherein a diameter of the circular base of the second portion is greater than a diameter of the threaded surface of the second end portion of the through hole.

\* \* \* \* \*